United States Patent
Katsuyama

(10) Patent No.: US 10,631,822 B2
(45) Date of Patent: Apr. 28, 2020

(54) ULTRASOUND DIAGNOSTIC DEVICE, ULTRASOUND DIAGNOSTIC METHOD AND ULTRASOUND DIAGNOSTIC PROGRAM STORAGE MEDIUM

(71) Applicant: FUJIFILM CORPORATION, Minato-ku, Tokyo (JP)

(72) Inventor: Kimito Katsuyama, Kanagawa (JP)

(73) Assignee: FIJIFILM CORPORATION, Tokyo (JP)

(*) Notice: Subject to any disclaimer, the term of this patent is extended or adjusted under 35 U.S.C. 154(b) by 920 days.

(21) Appl. No.: 14/533,089

(22) Filed: Nov. 5, 2014

(65) Prior Publication Data

US 2015/0057543 A1 Feb. 26, 2015

Related U.S. Application Data

(63) Continuation of application No. PCT/JP2013/064496, filed on May 24, 2013.

(30) Foreign Application Priority Data

May 25, 2012 (JP) .................. 2012-120213

(51) Int. Cl.
- *A61B 8/08* (2006.01)
- *A61B 8/00* (2006.01)
- *A61B 8/14* (2006.01)

(52) U.S. Cl.
CPC ............ *A61B 8/085* (2013.01); *A61B 8/4488* (2013.01); *A61B 8/5207* (2013.01);
(Continued)

(58) Field of Classification Search
None
See application file for complete search history.

(56) References Cited

U.S. PATENT DOCUMENTS 4,872,346 A * 10/1989 Kelly-Fry ............ A61B 8/0825
73/627
5,997,477 A * 12/1999 Sehgal ................. A61B 8/0825
600/437

(Continued)

FOREIGN PATENT DOCUMENTS

JP   H03-24868 A    2/1991
JP   H06-105841 A   4/1994
(Continued)

OTHER PUBLICATIONS

Written Opinion of the ISA issued in International Application No. PCT/JP2013/064496 dated Jul. 30, 2013.
(Continued)

*Primary Examiner* — Katherine L Fernandez
(74) *Attorney, Agent, or Firm* — Solaris Intellectual Property Group, PLLC

(57) ABSTRACT

An ultrasound diagnostic device includes an ultrasound probe including ultrasound transducers that transmit ultrasound toward an imaging subject, receive ultrasound reflected from the imaging subject, and output ultrasound detection signals; an alteration unit that alters a transmission frequency of the transmitted ultrasound or a reception frequency of the received ultrasound, from a frequency for converting amplitudes, of the ultrasound detection signals outputted from the ultrasound probe, into an intensity distribution of brightnesses and displaying the distribution, to a frequency for carrying out diagnosis of tissue characteristics; and a calculation unit that calculates an index for diagnosing tissue characteristics, based on a relationship between received signals, at a time when the transmission frequency or the reception frequency is altered to a frequency at which diagnosis of tissue characteristics is carried (Continued)

out, at two or more different ultrasound transducers at the ultrasound probe.

12 Claims, 12 Drawing Sheets

(52) U.S. Cl.
CPC .............. *A61B 8/5223* (2013.01); *A61B 8/14* (2013.01); *A61B 8/463* (2013.01)

(56) References Cited

U.S. PATENT DOCUMENTS

| | | | | |
|---|---|---|---|---|
| 6,585,647 | B1* | 7/2003 | Winder | A61B 8/08 128/916 |
| 7,500,956 | B1* | 3/2009 | Wilk | A61B 5/6843 600/439 |
| 8,376,947 | B2* | 2/2013 | Rambod | A61B 8/0825 382/131 |
| 2007/0239005 | A1* | 10/2007 | Ogasawara | A61B 8/14 600/437 |
| 2008/0242979 | A1* | 10/2008 | Fisher | A61B 6/4233 600/427 |
| 2013/0116564 | A1 | 5/2013 | Katsuyama | |
| 2013/0123628 | A1 | 5/2013 | Katsuyama | |

FOREIGN PATENT DOCUMENTS

| | | |
|---|---|---|
| JP | 2001-238884 A | 9/2001 |
| JP | 2005-125081 A | 5/2005 |
| JP | 2006-255014 A | 9/2006 |
| JP | 2007-7045 A | 1/2007 |
| JP | 2010-051553 A | 3/2010 |
| JP | 2010-99452 A | 5/2010 |
| WO | 2012/002420 A | 1/2012 |
| WO | 2012/002421 A | 1/2012 |

OTHER PUBLICATIONS

International Search Report issued in International Application No. PCT/JP2013/064496 dated Jul. 30, 2013.

Acoustic Characteristics of the Tissue and the Ultrasonic B-mode Image, Hiroyuki Hachiya, Medical Imaging Technology, vol. 21 No. 2, Mar. 2003.

"Tissue characterization by sound velocity measurements", Kouichi Akamatsu, "Rinshou'i", vol. 12, No. 11, 1986.

"Cho'onpa Binran" (Ultrasound handbook), published by Maruzen, 1999.

English language translation of the following: Office action dated Nov. 4, 2015 from the JPO in a Japanese patent application corresponding to the instant patent application.

* cited by examiner

ULTRASOUND DIAGNOSTIC DEVICE, ULTRASOUND DIAGNOSTIC METHOD AND ULTRASOUND DIAGNOSTIC PROGRAM STORAGE MEDIUM

CROSS-REFERENCE TO RELATED APPLICATIONS

This application is a continuation application of International Application No. PCT/JP2013/064496, filed on May 24, 2013. Further, this application claims priority from Japanese Patent Application No. 2012-120213, filed on May 25, 2012. The disclosures of the above-referenced applications are incorporated by reference herein in their entireties.

BACKGROUND OF THE INVENTION

Field of the Invention

The present invention relates to an ultrasound diagnostic device, an ultrasound diagnostic method and an ultrasound diagnostic program storage medium, and in particular, relates to an ultrasound diagnostic device, an ultrasound diagnostic method and an ultrasound diagnostic program medium that transmit and receive ultrasound waves to and from a diagnosis region of an imaging subject, and carry out diagnosis of tissue characteristics of the imaging subject on the basis of a relationship of received signals of the transmitted ultrasound waves.

Related Art

There are conventionally known ultrasound diagnostic devices that capture and display ultrasound images by transmitting and receiving ultrasound waves to and from a diagnosis region of an imaging subject by using ultrasound waves. Various attempts have been made in the application thereof to diagnoses, such as the diagnoses of characteristics of the internal structure and structural components and the like of imaging subject tissue, and the discrimination of tissue and lesions and the like, on the basis of the ultrasound images.

For example, Japanese Patent Application Laid-Open (JP-A) No. 2005-125081 discloses an ultrasound diagnostic device that has a B-mode image data generating section that generates first image data on the basis of the intensities of detection signals that are obtained by transmitting and receiving ultrasound waves having plural frequency components, frequency component extracting sections that extract at least one frequency component from the detection signals, a frequency image data generating section that generates second image data on the basis of the intensity of the at least one frequency component that has been extracted, and an image selecting section that selects at least one of the first image data or the second image data.

Further, JP-A No. 2001-238884 discloses an ultrasound diagnostic device that is equipped with specifying means, transmitting and receiving means, and quantity analyzing means. The specifying means specifies an analysis region at a portion within a tomographic image. The transmitting and receiving means transmits ultrasound pulses at an imaging subject portion corresponding to the analysis region in accordance with transmission conditions for quantity analysis, and receives echo signals produced from the imaging subject portion in response to the transmissions. The quantity analyzing means quantitatively analyzes a tissue characteristic on the basis of the echo signals.

However, although the technique disclosed in JP-A No. 2005-125081 focuses on the frequency characteristics of the transmittivity of the tissue and can display ultrasound images of a high SN ratio, there is room for improvement in carrying out highly-accurate diagnosis of tissue characteristics.

Further, the technique disclosed in JP-A No. 2001-238884 focuses on the scattering structure of a lesion being greatly uneven, and analyzes the degree of deviation from the Rayleigh distribution of the brightness values, and thereby quantifies and diagnoses the normality/abnormality of the tissue. However, there is room for improvement in carrying out more highly-accurate diagnosis of tissue characteristics.

SUMMARY

The present invention has been made in consideration of the above-described circumstances, and provides an ultrasound diagnostic device, an ultrasound diagnostic method and an ultrasound diagnostic program storage medium that make highly-accurate diagnosis of tissue characteristics possible.

Solution to Problem

An aspect of the present invention is an ultrasound diagnostic device including: an ultrasound probe including a plurality of ultrasound transducers that transmit ultrasound toward an imaging subject, receive ultrasound reflected from the imaging subject, and output ultrasound detection signals; an alteration unit that alters a transmission frequency of the ultrasound transmitted from the ultrasound probe or a reception frequency of the ultrasound received by the ultrasound probe, from a frequency for converting amplitudes, of the ultrasound detection signals outputted from the ultrasound probe, into an intensity distribution of brightnesses and displaying the distribution, to a frequency for carrying out diagnosis of tissue characteristics; and a calculation unit that calculates an index for diagnosing tissue characteristics, based on a relationship between received signals, at a time when the transmission frequency or the reception frequency is altered by the alteration unit to a frequency at which diagnosis of tissue characteristics is carried out, at two or more different ultrasound transducers at the ultrasound probe.

In accordance with the ultrasound diagnostic device of the present aspect, ultrasound is transmitted to an imaging subject by the plural ultrasound transducers of the ultrasound probe, and the ultrasound reflected by the imaging subject is received.

Further, the alteration unit changes the transmission frequency of the ultrasound transmitted from the ultrasound probe, or the reception frequency, to different frequencies for a case of a B-mode in which the amplitudes of the ultrasound detection signals are converted into intensities of brightnesses and are displayed, and a case of carrying out diagnosis of tissue characteristics.

Further, the calculation unit calculated an index for diagnosing tissue characteristics, on the basis of a relationship of received signals at a time when the transmission frequency or the reception frequency is changed by the alteration unit to the frequency at which diagnosis of tissue characteristics is carried out, at two or more different ultrasound transducers. Due thereto, micro structural changes in sound velocity or attenuation due to a lesion can be captured, and carrying out diagnosis of tissue characteristics becomes possible. Further, since the transmission frequency or the reception frequency is changed to a frequency that is suited to the diagnosing of tissue characteristics when carrying out diagnosis of tissue characteristics, non-uniformity of micro-structures can be measured highly accurately.

At a time of diagnosing tissue characteristics, the alteration unit may alter the transmission frequency of the ultrasound transmitted from the ultrasound probe to a transmission frequency that is set in advance in accordance with depth and size of a region to be observed, or, at a time of diagnosing tissue characteristics, the alteration unit may alter reception frequencies of the ultrasound detection signals received by the ultrasound probe to a frequency that is set in advance in accordance with depth and size of a region to be observed.

Further, the calculation unit may calculate the index by evaluating non-uniformity of an acoustic characteristic based on a relationship between received signals of two or more ultrasound transducers whose ultrasound differ at a region of interest that is set in advance, or, may determine sound velocity or attenuation at least at one point of interest within a pre-specified region of interest, and calculates the index based on the determined sound velocity or attenuation.

Moreover, the aspect may further include a display unit that displays the index calculated by the calculation unit.

Another aspect of the present invention is an ultrasound diagnostic method comprising: when diagnosing tissue characteristics, altering a transmission frequency of ultrasound transmitted from an ultrasound probe that includes a plurality of ultrasound transducers that transmit ultrasound toward an imaging subject, receive ultrasound reflected from the imaging subject, and output ultrasound detection signals, or a reception frequency of ultrasound received by the ultrasound probe, from a frequency for converting amplitudes of the ultrasound detection signals outputted from the ultrasound probe into an intensity distribution of brightnesses and displaying the distribution, to a different frequency for carrying out diagnosis of tissue characteristics; and calculating an index for diagnosing tissue characteristics, based on a relationship between received signals, at a time when the transmission frequency or the reception frequency is altered to a frequency in a case of carrying out diagnosis of tissue characteristics, at two or more different ultrasound transducers at the ultrasound probe.

In accordance with the ultrasound diagnostic method of the present aspect, when diagnosing tissue characteristics, the transmission frequency of ultrasound transmitted from the ultrasound probe, or the reception frequency, is changed from the frequency of the case of B-mode in which amplitudes of the ultrasound detection signals are converted into intensities of brightnesses and are displayed, to a different frequency of the case of carrying out diagnosis of tissue characteristics.

Further, an index for diagnosing tissue characteristics is calculated on the basis of a relationship of received signals at a time when the transmission frequency or the reception frequency is changed to the frequency in the case of carrying out diagnosing of tissue characteristics, at two or more different ultrasound transducers. Due thereto, micro structural changes in sound velocity or attenuation due to a lesion can be captured, and carrying out diagnosis of tissue characteristics becomes possible. Further, since the transmission frequency or the reception frequency is changed to a frequency that is suited to the diagnosing of tissue characteristics when carrying out diagnosis of tissue characteristics, non-uniformity of micro-structures can be measured highly accurately.

The altering may include, at a time of diagnosing tissue characteristics, altering the transmission frequency of the ultrasound transmitted from the ultrasound probe to a transmission frequency that is set in advance in accordance with depth and size of a region to be observed, or, may include, at a time of diagnosing tissue characteristics, changing reception frequencies of the ultrasound detection signals received by the ultrasound probe to a frequency that is set in advance in accordance with depth and size of a region to be observed.

The calculation may include calculating the index by evaluating non-uniformity of an acoustic characteristic based on a relationship of received signals of two or more ultrasound transducers whose ultrasound differ at a region of interest that is set in advance, or the calculation may include determining sound velocity or attenuation at least at one point of interest within a pre-specified region of interest, and calculating the index based on the determined sound velocity or attenuation.

Moreover, the calculated index may be displayed at a display unit.

Yet another aspect of the present invention is a non-transitory storage medium storing a program that causes a computer to execute ultrasound diagnostic processings, the processings comprising: when diagnosing tissue characteristics, altering a transmission frequency of ultrasound transmitted from an ultrasound probe that includes a plurality of ultrasound transducers that transmit ultrasound toward an imaging subject, receive ultrasound reflected from the imaging subject, and output ultrasound detection signals, or a reception frequency of ultrasound received by the ultrasound probe, from a frequency in a case of converting amplitudes of the ultrasound detection signals outputted from the ultrasound probe into an intensity distribution of brightnesses and displaying the distribution, to a different frequency in a case of carrying out diagnosis of tissue characteristics; and calculating an index for diagnosing tissue characteristics, based on a relationship between received signals, at a time when the transmission frequency or the reception frequency is altered to a frequency in a case of carrying out diagnosis of tissue characteristics, at two or more different ultrasound transducers at the ultrasound probe.

In accordance with the ultrasound diagnostic program of the present aspect, when diagnosing tissue characteristics, the transmission frequency of ultrasound transmitted from the ultrasound probe, or the reception frequency, is changed from the frequency of the case of B-mode in which amplitudes of the ultrasound detection signals are converted into intensities of brightnesses and are displayed, to a different frequency of the case of carrying out diagnosis of tissue characteristics.

Further, an index for diagnosing tissue characteristics is calculated on the basis of a relationship of received signals at a time when the transmission frequency or the reception frequency is changed to the frequency in the case of carrying out diagnosing of tissue characteristics, at two or more different ultrasound transducers. Due thereto, micro structural changes in sound velocity or attenuation due to a lesion can be captured, and carrying out diagnosis of tissue characteristics becomes possible. Further, the transmission frequency or the reception frequency is changed to a frequency that is suited to the diagnosing of tissue characteristics when carrying out diagnosis of tissue characteristics, non-uniformity of micro-structures can be measured highly accurately.

The altering may include, at a time of diagnosing tissue characteristics, altering the transmission frequency of the ultrasound transmitted from the ultrasound probe to a transmission frequency that is set in advance in accordance with depth and size of a region to be observed, or may include, at a time of diagnosing tissue characteristics, altering the reception frequency of the ultrasound detection signals received by the ultrasound probe to a frequency that is set in advance in accordance with depth and size of a region to be observed.

Further, the calculation may include calculating the index by evaluating non-uniformity of an acoustic characteristic based on a relationship between received signals of two or more ultrasound transducers whose ultrasound differ at a region of interest that is set in advance, or may include determining sound velocity or attenuation at least at one point of interest within a pre-specified region of interest, and calculating the index based on the determined sound velocity or attenuation.

Moreover, the calculated index may be displayed at a display unit.

As described above, in the present aspects, highly-accurate diagnosis of tissue characteristics is possible by calculating an index for diagnosing tissue characteristics on the basis of received signals of ultrasound at the time when the frequency is changed to a frequency at which diagnosis of tissue characteristics is carried out.

BRIEF DESCRIPTION OF THE DRAWINGS

Exemplary embodiments will be described in detail based on the following figures.

DETAILED DESCRIPTION

First Embodiment

Figure 1:
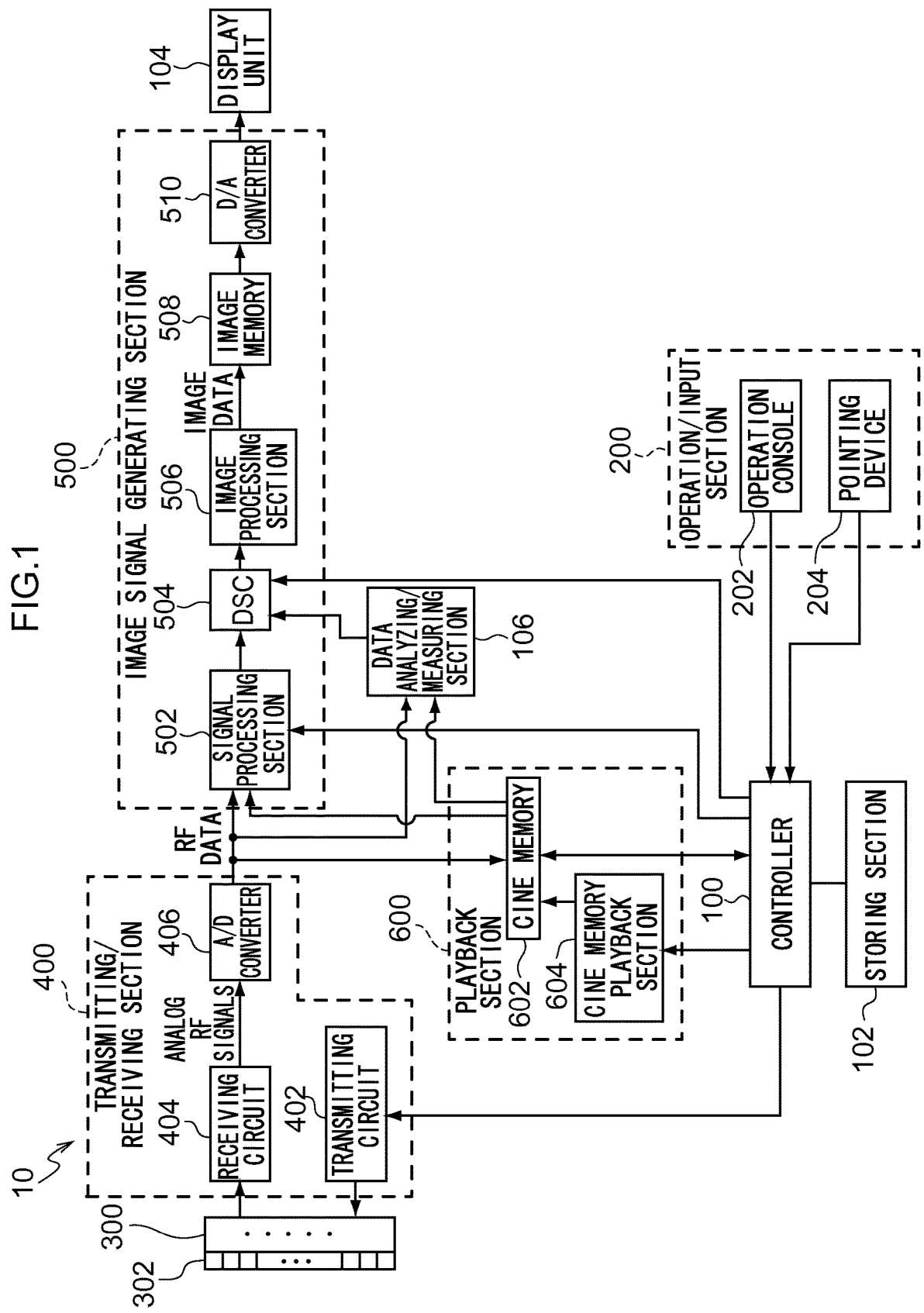
FIG. 1 is a block diagram showing the schematic structure of an ultrasound diagnostic device of a first exemplary embodiment.

FIG. 1 is a block diagram showing the schematic structure of an ultrasound diagnostic device relating to a first exemplary embodiment.

As shown in FIG. 1, an ultrasound diagnostic device 10 relating to the present embodiment transmits ultrasound beams to an imaging subject from an ultrasound probe 300, receives ultrasound beams (ultrasound echoes) that are reflected by the imaging subject, generates and displays ultrasound images from detection signals of the ultrasound echoes.

A controller 100 is structured by a computer having an unillustrated CPU (Central Processing Unit), ROM (Read Only Memory), RAM (Random Access Memory), input/output port and the like, and carries out control of the respective blocks of the ultrasound diagnostic device 10 in accordance with operational inputs from an operation input section 200.

The operation input section 200 is an input device that accepts operation inputs from an operator (a user). The operation input section 200 includes a console 202 and a pointing device 204. The console 202 includes a keyboard for inputting text information (for example, patient information) and the like, and a display mode switching button, a freeze button, a cine-memory replay button, an analysis and measurement button and the like. The display mode switching button is for switching between various display modes, such as a mode that displays individual amplitude images (B-mode images), a mode that displays the results of determinations of local sound velocity values, and the like. The freeze button is for instructing switching between a live mode and a freeze-frame mode. The cine-memory replay button is for instructing a cine-memory replay. The analysis and measurement button is for instructing analysis and measurement of an ultrasound image. The pointing device 204 is a device for designating a region in a screen of a display unit 104. For example, a track ball, a mouse or the like may be used as the pointing device 204. A touch panel may also be used as the pointing device 204.

A storage section 102 stores various control programs through which the controller 100 controls the blocks of the ultrasound diagnostic device 10. For example, a hard disc, a semiconductor memory or the like may be used as the storage section 102.

As the display unit 104, various display devices such as, for example, a cathode ray tube (CRT) display, a liquid crystal display or the like may be used. The display unit 104 displays ultrasound images (video images and still images) and various settings screens and the like.

The ultrasound probe 300 is a probe that is used by being touched against an imaging subject. The ultrasound probe 300 is equipped with plural ultrasound transducers 302 that structure a one-dimensional or two-dimensional transducer array. A transmission and reception section 400 is connected to the ultrasound transducers 302.

The transmission and reception section 400 is equipped with a transmission circuit 402, a reception circuit 404 and an A/D converter 406. The ultrasound transducers 302 transmit an ultrasound beam at the imaging subject in accordance with driving signals applied by the transmission circuit 402 of the transmission and reception section 400, the reception circuit 404 receives ultrasound echoes reflected from the imaging subject, and detection signals are converted to digital signals by the A/D converter 406 and are outputted.

The ultrasound transducers 302 include oscillators that are structured with electrodes being formed at opposite ends of a material with piezoelectric characteristics (a piezoelectric material). As the piezoelectric material structuring these oscillators, for example, a piezoelectric ceramic such as PZT (lead (Pb) zirconate titanate), or a polymer piezoelectric material such as PVDF (polyvinylidene difluoride) may be used. When electronic signals are sent to the electrodes of the oscillators and voltages are applied, the piezoelectric materials expand and contract, and ultrasonic waves are produced at the oscillators by these expansions and contractions of the piezoelectric materials. As examples, if pulse-shaped electronic signals are sent to the oscillator electrodes, pulse-shaped ultrasonic waves are produced, and if continuous-wave electronic signals are sent to the oscillator electrodes, continuous-wave ultrasonic waves are produced. The ultrasonic waves produced at the oscillators combine to form an ultrasound beam. When ultrasonic waves are received by the oscillators, the piezoelectric materials of the oscillators expand and contract and generate electronic signals. The electronic signals generated at the oscillators are outputted to the reception circuit 404 to serve as ultrasound detection signals.

In the present exemplary embodiment, the transmission frequency of the ultrasound probe 300 that is used is alterable. For example, a probe that employs ultrasound transducers with a wide-band frequency characteristic—using compound-type piezoelectric elements—and produces plural types of ultrasound with different frequency ranges and central frequencies from individual ultrasound transducers may be used. As another example, plural types of ultrasound transducer with different frequency characteristics may be provided and switched between for use.

The digital signals outputted from the A/D converter 406 of the transmission and reception circuit 400 are outputted to a replay section 600 and an image signal generating section 500.

The image signal generation section 500 is provided with a signal processing section 502, a digital scan converter (DSC) 504, an image processor 506, an image memory 508 and a D/A converter 510. The respective functions thereof are described in detail below.

Now, ultrasound diagnostic processing in the live mode is described. The live mode is a mode in which an ultrasound image (a video image) obtained by touching the ultrasound probe 300 against an imaging subject and transmitting and receiving ultrasound is displayed, and is analyzed and measured.

An ultrasound diagnosis is started by the ultrasound probe 300 being touched against an imaging subject and a user operating the operation input section 200 to give an operation start instruction. After the ultrasound diagnosis is started, the controller 100 outputs control signals to the transmission and reception section 400, and the transmission of an ultrasound beam at the imaging subject and the reception of ultrasound echoes from the imaging subject are commenced. The controller 100 specifies an ultrasound beam transmission direction and an ultrasound echo reception direction for each of the ultrasound transducers 302.

Then, the controller 100 selects a transmission delay pattern in accordance with the ultrasound beam transmission direction and selects a reception delay pattern in accordance with the ultrasound echo reception direction. The term "transmission delay pattern" is intended to include data of a pattern of delay durations that are applied to driving signals in order to form an ultrasound beam in the desired direction of the ultrasonic waves transmitted from the plural ultrasound transducers 302. The term "reception delay pattern" is intended to include data of a pattern of delay durations of reception by the plural ultrasound transducers 302. Transmission delay patterns and reception delay patterns are stored in the storage section 102 in advance. The controller 100 selects a transmission delay pattern and a reception delay pattern from the transmission delay patterns and reception delay patterns stored in the storage section 102, and outputs control signals to the transmission and reception section 400 to control the transmission and reception of ultrasonic waves in accordance with the selected transmission delay pattern and reception delay pattern.

The transmission circuit 402 generates driving signals in accordance with the control signals from the controller 100, and applies the driving signals to the ultrasound transducers 302. The transmission circuit 402 delays the driving signals being applied to the respective ultrasound transducers 302 in accordance with the transmission delay pattern selected by the controller 100. Thus, the transmission circuit 402 implements transmission focusing that adjusts (delays) the timings of application of the driving signals to the ultrasound transducers 302 such that the ultrasonic waves transmitted from the plural ultrasound transducers 302 form the ultrasound beam. The timings of application of the driving signals may also be adjusted such that the ultrasonic waves transmitted from the plural ultrasound transducers 302 at one time reach the whole of an imaging region of the imaging subject.

The reception circuit 404 receives and amplifies the ultrasound detection signals outputted from the ultrasound transducers 302. As mentioned above, since distances between the ultrasound transducers 302 and an ultrasound reflection source within the imaging subject are respectively different, durations that the reflected waves take to reach the ultrasound transducers 302 are also different. The reception circuit 404 is equipped with delay circuits, which delay the detection signals by amounts corresponding to differences (delay durations) between the arrival times of the reflected waves in accordance with a sound velocity (hereinafter referred to as "the assumed sound velocity") or a distribution of sound velocities, which amounts are specified on the basis of the reception delay pattern selected by the controller 100. Subsequently, the reception circuit 404 performs reception focusing processing by performing matching addition of the detection signals to which the delay durations have been applied. In a case in which there is a separate ultrasound reflection source at a different position from an ultrasound reflection source XROI that is the target, ultrasound detection signals from the separate ultrasound reflection source have different arrival times. Therefore, the phases of the ultrasound detection signals from the separate ultrasound reflection source are cancelled out by addition at an addition circuit in the reception circuit 404. Thus, reception signals from the ultrasound reflection source XROI are strongest and are in focus. This reception focusing processing forms acoustic ray signals (hereinafter referred to as "RF signals") in which the ultrasound echoes have a sharp focusing point.

The A/D converter 406 converts the analog RF signals outputted from the reception circuit 404 to digital RF signals (hereinafter referred to "RF data"). This RF data includes phase information of the received waves (carrier waves). The RF data outputted from the A/D converter 406 is inputted to both the signal processing section 502 and a cine-memory 602.

The cine-memory 602 sequentially stores the RF data inputted from the A/D converter 406. The cine-memory 602 also stores information relating to frame rates in association with the RF data (for example, parameters representing the depth of an ultrasound reflection position, the density of scanning lines, and the size of the field of view), which information is inputted from the controller 100.

The signal processing section 502 corrects attenuation with distance of the RF data, in accordance with the depth of the ultrasound reflection position, using sensitivity time gain control (STC), and then applies envelope detection processing to the RF data and creates B-mode image data (image data in which the amplitudes of ultrasound echoes are represented by point brightnesses (luminances)).

The B-mode image data created by the signal processing section 502 is provided in a different scanning system from the scanning system of ordinary television signals. Accordingly, the DSC 504 converts (raster conversion) the B-mode image data to usual image data (for example, image data in a television signal scanning system (the NTSC system)). The image processor 506 applies various kinds of image processing (for example, contrast processing) to the image data inputted from the DSC 504 as necessary.

The image memory 508 stores the image data inputted from the image processor 506. The D/A converter 510 converts image data read from the image memory 508 to analog image signals and outputs the analog image signals to the display unit 104. Thus, the ultrasound image (video image) captured by the ultrasound probe 300 is displayed at the display unit 104.

In the present exemplary embodiment, the RF signals are detection signals to which the reception focusing processing has been applied in the reception circuit 404. However, detection signals to which the reception focusing processing has not been applied may also be used as RF signals. In this case, the plural ultrasound detection signals outputted from the plural ultrasound transducers 302 are amplified at the reception circuit 404, and RF data is generated by the amplified detection signals, which is to say the RF signals, being A/D-converted at the A/D converter 406. This RF data is both provided to the signal processing section 502 and stored in the cine-memory 602. The reception focusing processing can be performed digitally at the signal processing section 502.

Now, the cine-memory replay mode is described. The cine-memory replay mode is a mode in which an ultrasound diagnostic image based on the RF data stored in the cine-memory 602 is displayed, and is analyzed and measured.

When the cine-memory replay button of the console 202 is pressed by a user, the controller 100 switches the operation mode of the ultrasound diagnostic device 10 to the cine-memory replay mode. In the cine-memory replay mode, the controller 100 instructs a cine-memory replay section 604 to replay RF data designated by operational inputs from the user. In accordance with the instructions from the controller 100, the cine-memory replay section 604 reads RF data from the cine-memory 602 and sends the RF data to the signal processing section 502 of the image signal generation section 500. The signal processing section 502, the DSC 504 and the image processor 506 apply predetermined processing (processing similar to the processing in the live mode) to the RF data sent from the cine-memory 602 to convert the RF data to image data, and then output the image data via the image memory 508 and the D/A converter 510 to the display unit 104. Thus, an ultrasound image (a video image or a still image) based on the RF data stored in the cine-memory 602 is displayed at the display unit 104.

In the live mode or the cine-memory replay mode, if the freeze button of the console 202 is pressed while an ultrasound image (a video image) is being displayed, the ultrasound image that is being displayed at the moment the freeze button is pressed is displayed as a still image at the display unit 104. Thus, a user may display a still image of a region of interest (ROI) and inspect the image.

If the measurement button of the console 202 is pressed, an analysis and/or measurement designated by operational inputs from the user is carried out. When the measurement button is pressed in the various operation modes, a data analysis and measurement section 106 acquires the RF data, before image processing is applied thereto, from the A/D converter 406 or the cine-memory 602, and uses this RF data to perform the analysis/measurement instructed by the user (for example, analyzing distortion of a tissue portion (a hardness diagnosis), measuring blood flow, measuring a movement of a tissue portion, or measuring an intima-media thickness (IMT) value). The data analysis and measurement section 106 also performs processing to calculate indices representing variations in sound velocity or attenuation. Analysis and measurement results from the data analysis and measurement section 106 are outputted to the DSC 504 of the image signal generation section 500. The DSC 504 incorporates the analysis and measurement results from the data analysis and measurement section 106 into the image data of the ultrasound image, and outputs the image data to the display unit 104. Thus, the ultrasound image and the analysis and measurement results are displayed at the display unit 104. In FIG. 1, the data analysis and measurement section 106 is illustrated as a separate component from the controller 100. However, the data analysis and measurement section 106 may be structured integrally with the controller 100 and provide the functions of data analysis and management as part of the functions of the controller 100. Herebelow, the data analysis and measurement section 106 is described as being part of the functions of the controller 100.

When the display mode switching button is pressed, the display mode is switched between the mode that displays individual B-mode images, a mode that displays sound velocity or attenuation variation determination results overlaid on a B-mode image (for example, a display in which color levels or brightnesses are altered in accordance with sound velocity or attenuation variations, or a display in which points at which sound velocity or attenuation variations are equal are joined by lines), and a mode in which a B-mode image and an image of sound velocity or attenuation variation determination results are displayed side by side. Thus, a user may, for example, find a lesion by inspecting the sound velocity or attenuation variation determination results.

Figure 12A:
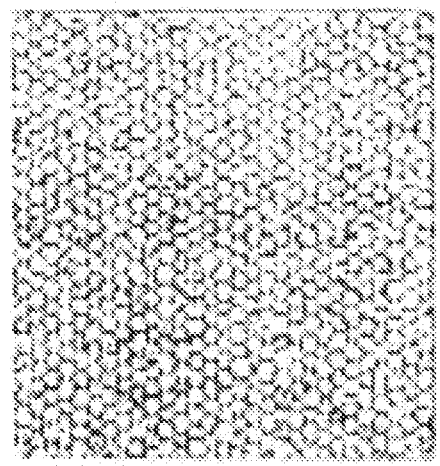
FIGS. 12A, 12B and 12C are drawings for explaining changes of a tissue characteristic in liver cirrhosis.
Figure 12B:
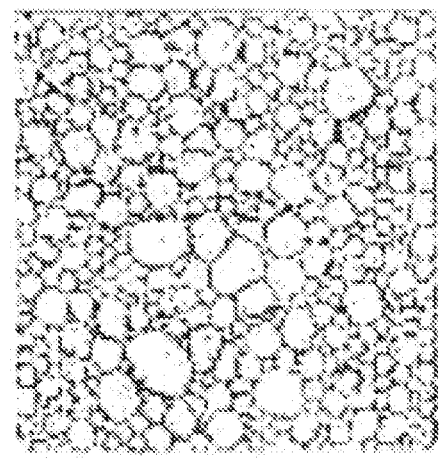
Figure 12C:
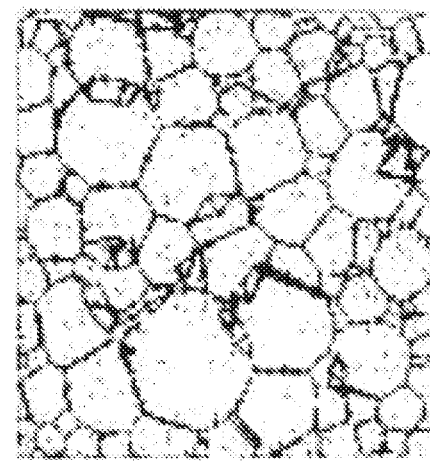

According to "Acoustic Characteristics of the Tissue and the Ultrasonic B-mode Image", Hiroyuki Hachiya, Medical Imaging Technology, Vol. 21 No. 2, March 2003, when a liver becomes cirrhotic, necrotic tissues connect together as the cirrhosis develops. As a result of repairs, surrounding tissues become fibrous and form nodules, and hepatic lobules are replaced with regenerative nodules. Examples of the distribution of scattering bodies are shown in FIG. 12A to FIG. 12C. FIG. 12A shows a normal liver. The respective hepatic lobules have random sizes of around 1.0 mm to 1.5 mm. As the liver develops moderate cirrhosis, as illustrated in FIG. 12B, numerous hepatic lobule structures are necrotized, fibrous tissues form, and nodule diameters increase to 3 mm to 4 mm. As lesions develop and the liver becomes severely cirrhotic, as illustrated in FIG. 12C, the nodule diameters grow to a maximum of around 7 mm. It has been reported that sound velocities, attenuation and scattering within these nodules are lower than in a normal liver, while fibrous portions have higher levels of micro-structural changes in sound velocity than a normal liver. On the other hand, according to "Tissue characterization by sound velocity measurements", Kouichi Akamatsu, "Rinshou'i", Vol. 12, No. 11, 1986, it has been found that there is no significant difference in macro sound velocity values between normal livers and cirrhotic livers. Therefore, it may not be possible to discern micro-structural changes in sound velocity or attenuation as described above by methods of macroscopic measurement of sound velocities or attenuation proposed in the related art.

Taking account of the above considerations, the ultrasound diagnostic device 10 of the present exemplary embodiment specifies a region of interest, measures variations in sound velocity or variations in attenuation of the region of interest, and diagnoses a tissue characteristic. As is described in more detail below, in the present exemplary embodiment, transmission focusing is applied to form a pseudo (dummy) point reflection. From the reception data of the respective elements (transducers), time differences are calculated from reception times approximated for a uniform sound velocity, and sound velocity variations are measured from variations in the time differences. Alternatively, attenuation (scattering and absorption) variations are measured from amplitude variations or frequency variations that are approximated for a uniform attenuation. The measured variations can then be used for diagnostics of a tissue characteristic.

Figure 2A:
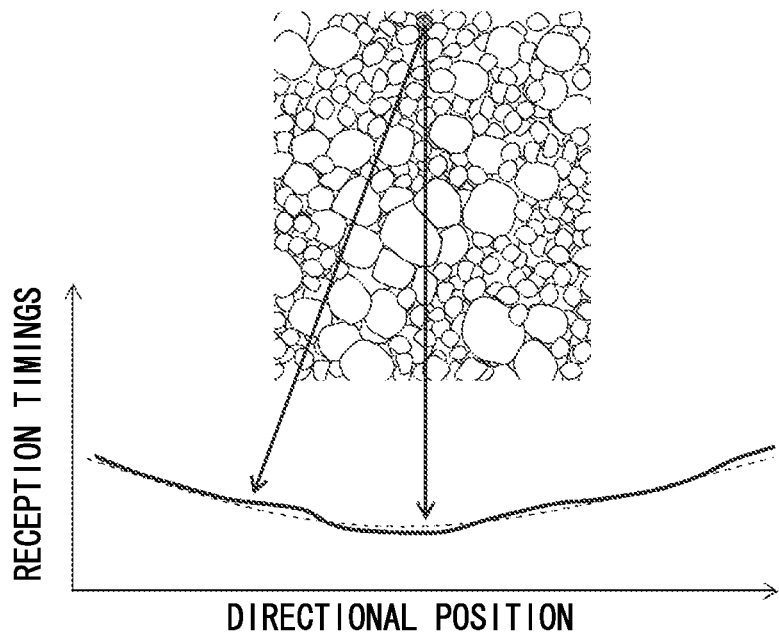
FIGS. 2A, 2B and 2C are explanatory drawings that schematically illustrate principles of measuring sound velocity variations and attenuation variations.
Figure 2B:
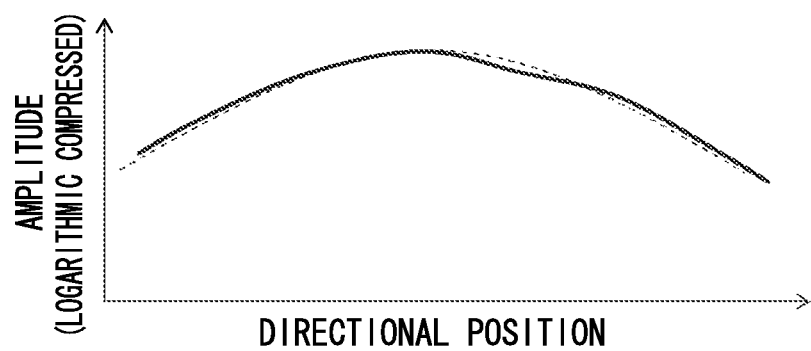
Figure 2C:
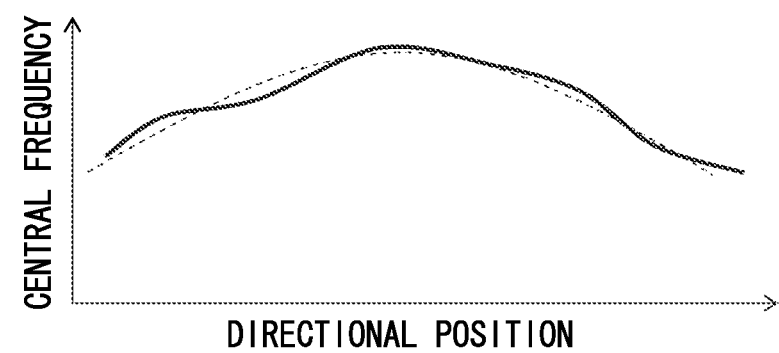

FIG. 2A to FIG. 2C schematically illustrate the principles of measuring sound velocity variations and attenuation variations.

FIG. 2A illustrates the measurement of sound velocity variations by finding variations from reception timings approximated for a uniform sound velocity. FIG. 2B illustrates the measurement of attenuation variations from amplitude variations approximated for a uniform attenuation. FIG. 2C illustrates the measurement of attenuation variations from central frequency variations approximated for a certain attenuation.

In each of these cases, transmission focusing is applied to form a pseudo point reflection, and sound velocity variations or attenuation variations are measured from the reception data of the respective elements.

That is, as shown in FIG. 2A, a pseudo point reflection is taken to be from a lattice point X of a region of interest ROI within an imaging subject. If cirrhosis has developed and nodules have formed, as illustrated in FIG. 2A, variations occur in the sound velocity and attenuation depending on directions of progress of the ultrasonic waves.

FIG. 2A shows a wavefront (reception timings) actually measured at the elements with a solid line, and shows a wavefront that is approximated assuming that the medium of the imaging subject has a uniform sound velocity with a broken line. Thus, FIG. 2A shows variations in reception timings caused by sound velocity variations at respective directional positions.

FIG. 2B shows logarithmically compressed values of amplitude actually measured at the elements with a solid line, and shows logarithmically compressed values of amplitude that are approximated assuming that the medium of the imaging subject has uniform attenuation with a broken line. Thus, FIG. 2B shows variations in logarithmically compressed values of amplitude caused by attenuation (absorption and dispersion) variations at the respective directional positions.

FIG. 2C shows central frequencies actually measured at the elements with a solid line, and shows central frequencies that are approximated assuming that the medium of the imaging subject has uniform attenuation with a broken line. Thus, FIG. 2C shows variations in the central frequency caused by attenuation (absorption and dispersion) variations at the respective directional positions.

Thus, reception timings, amplitudes and central frequencies of received waves from a pseudo point reflection formed by applying transmission focusing feature vary from reception timings, amplitudes and central frequencies when uniform sound velocity and uniform attenuation are assumed. This is because the mixing proportions of media with different sound velocities and attenuations vary between different paths corresponding to directional positions. In a case in which the mixing proportions of media with different sound velocities and attenuations vary between different paths, variations in timings, amplitudes and frequencies of the reception signals arise in the process of propagation from the pseudo point reflection to the elements, and are also caused by interference between adjacent ultrasound waves when the pseudo point reflection is formed. In specific terms, the transmission focusing does not concentrate at a single point, because of the sound velocity and attenuation (including scattering) varying between different paths. Consequently, there is interference from scattering of adjacent ultrasound waves, as a result of which variations in the timings, amplitudes and frequencies of the reception signals occur. It can be easily understood from FIG. 2A to FIG. 2C that the greater the variations in mixing proportions between different paths, the greater the variations in reception timings, amplitudes and central frequencies between directional positions, and also that the greater a spatial frequency of variations in the mixing proportions between the different paths, the greater a spatial frequency of the variations in reception timings, amplitudes and central frequencies between directional positions.

Therefore, information about the magnitudes and spatial frequencies of variations in the mixing proportions of media with different sound velocities and attenuations in a region of interest may be acquired from the magnitudes and spatial frequencies of variations in the reception timings, amplitudes or central frequencies of reflected waves from a lattice point X, compared with the reception timings, amplitudes or central frequencies that would be obtained if uniform sound velocity and uniform attenuation are assumed.

Hence, variations in sound velocity or attenuation may be determined, and this may be used for diagnostics of tissue characteristics. Herein, the embodiment is described using the example of cirrhosis, but it will be clear that application of the embodiments is not limited to cirrhosis.

Herebelow, processing to find an index representing sound velocity variations or attenuation variations (a variation index) is described.

First, a method of determining sound velocity variations is described.

In order to simplify explanation, it is assumed that two kinds of media are present on a particular path when ultrasound is being propagated from a sound source to an element. This situation is schematically illustrated in FIG. 3.

Figure 3:
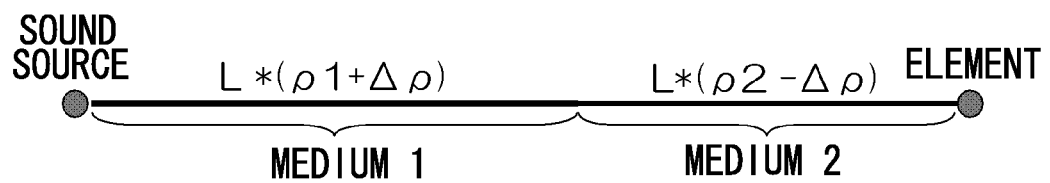
FIG. 3 is a schematic drawing for explaining a situation in which two different media exist on a path from a sound source to an element.

In reality, a medium 1 and a medium 2 would not be clearly separated as is shown in FIG. 3 but mixed together along a path in a complicated manner. FIG. 3 illustrates a case in which medium 1 and medium 2 are each gathered together in one direction and the mixing proportions thereof can be easily seen.

In FIG. 3, L represents the entire length of the path (path length) from the sound source to the element, ρ1 and ρ2 represent the average mixed proportions of medium 1 and medium 2 independent of propagation paths, and Δρ represents the amount of change in the mixed proportion depending on the path.

On the path shown in FIG. 3, if it is assumed that a mixing ratio of medium 1 and medium 2 differs from the average mixing ratio ρ1: ρ2 by Δρ, becoming (ρ1+Δρ):(ρ2−Δρ), then of the overall length L of the path, the length occupied by medium 1 is L×(ρ1+Δρ) and the length occupied by medium 2 is L×(ρ2−Δρ).

If the sound velocity of the ultrasound in medium 1 is $v_1$ and the sound velocity of the ultrasound in medium 2 is $v_2$, then a reception timing t at which ultrasound emitted from the sound source is received by the element is given by the following expression.

$$t = L \times (\rho 1 + \Delta \rho)/v_1 + L \times (\rho 2 + \Delta \rho)/v_2$$
$$= L \times (1/v_1) \times \rho 1 + L \times (1/v_2) \times \rho 2 + L \times \Delta \rho \times ((1/v_1) - (1/v_2))$$

If a reception timing that does not depend on the path (i.e., does not take account of path variations)

$$(L \times (1/v_1) \times \rho 1 + L \times (1/v_2) \times \rho 2)$$

is subtracted, an amount of change of the reception timing depending on the path is obtained by the following expression.

$$L \times \Delta \rho \times ((1/v_1) - (1/v_2))$$

If this is then divided by the total length of the path (the path length) L, the following expression (1) is obtained to serve as an index that is independent of the path length L.

$$\Delta \rho \times ((1/v_1) - (1/v_2)) \qquad (1)$$

However, because the change in the mixing proportions Δρ over the path length L varies between different paths, the index represented by the above expression (1) varies between different paths.

Therefore, a variation index that is independent of paths may be obtained by finding the standard deviation of values of expression (1) for all paths.

The change Δρ in the mixing proportions varies more greatly in accordance with pathological changes of tissues, or the difference between $v_1$ and $v_2$ increases with pathological changes of tissues. Therefore, a variation index based on expression (1) is an index that excellently represents a degree of variations.

Only two types of medium have been considered hereabove. However, in any case in which there are two or more types of medium, the index (1) of two or more types is the sum of the changes of the mixing proportions of the different media—Δρ1, Δρ2, etc.—so the degree of variations thereof is an index that excellently represents a degree of pathological changes.

In the above method, reception timings, and reception timings and path lengths that do not take account of path variations, are unknown.

Among these, the reception timings (the reception timings at the elements) may be found using a known phase aberration analysis technique (for example, see JP-A No. H6-105841). That is, phase differences in reception signals of the reference signal at the elements of the ultrasound probe are detected using a constant signal as a reference signal, the phase difference detection results of neighboring elements are compared, and the differences therebetween are represented by "D". Then, in a graph in which element identification numbers of the ultrasound probe are plotted on the horizontal axis and phase differences between the reception signals at the elements and the reference signal S are plotted on the vertical axis, 360° is added to points that are not continuous between the positive side and the negative side (that is, where the difference D is below −180°), and 360° is subtracted from points that are not continuous between the negative side and the positive side (that is, where the difference D is above +180°), to make a non-continuous line into a continuous line. Thus, phase aberrations may be accurately detected over a wide range.

The reception timings that do not take account of path variations may be resolved into the path length L and (1/average sound velocity)=$((1/v_1) \times \rho 1 + (1/v_2) \times \rho 2)$.

Now, a method of finding the path length L and an average sound velocity is described.

Figure 4:
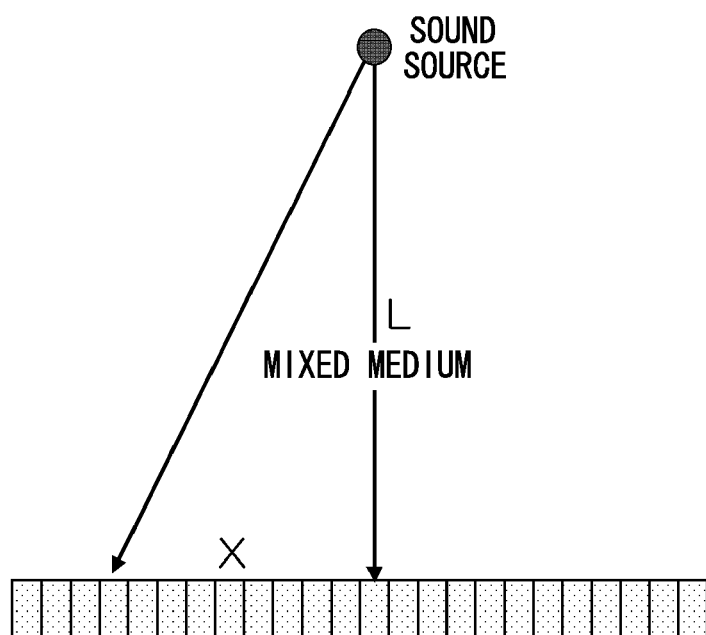
FIG. 4 is a drawing for explaining how a path length and an average sound velocity in a mixed medium are found.

As shown in FIG. 4, a sound source within a target formed of a number of types of media with different sound velocities (a mixed medium) is assumed to be at a depth that is the distance L from the element surfaces.

First, a sound velocity (average sound velocity) and depth, which are found assuming that the medium as far as the sound source is uniform, are calculated from the element reception signals of ultrasonic waves emitted from the sound source, illustrated in FIG. 4.

A reception timing T(X) at an element that is at a position a distance X from being directly in front of the sound source, as shown in FIG. 4, may be given by the following expression.

$$T(X) = \sqrt{(L_2 + X_2)} \times ((1/v_1) \times \rho 1 + (1/v_2) \times \rho 2 + (1/v_3) \times \rho 3 + \ldots) \qquad (2)$$

Here, the symbol √(A) represents the square root of A, and ρn and $v_n$ represent the mixing proportion and sound velocity of each medium n. The mixing proportions herein do not include the changes Δρ.

Because ρn is considered to be constant regardless of the propagation path, the average sound velocity that is assumed to be uniform and the depth in the above expression (2) can be uniquely calculated, as in the following expression (3).

$$1/\text{average sound velocity} = ((1/v_1) \times \rho 1 + (1/v_2) \times \rho 2 + (1/v_3) \times \rho 3 + \ldots)$$

$$\text{Depth} = L \qquad (3)$$

The average sound velocity in the above expression (3) is the aforementioned average sound velocity. The respective path lengths may be found from the depth L and the element positions X.

That is, the average sound velocity and respective path lengths may be calculated by considering the element reception timings all together. Even if the changes Δρ in the mixing proportions according to the respective paths are taken account of, any effect thereof is likely to be small when the element signals are considered all together.

A known image analysis technique (for example, see JP-A No. 2007-7045) may be used to find the average sound velocity and the depth. This method assumes values for the average sound velocity (and the depth) and finds a value at which the sharpness, contrast or the like of an image of the sound source is maximized.

As a further alternative, a method is also possible in which the element reception timings are found from phase aberration analysis, then an average reception timing is found using a least squares fit, and an average sound velocity (and depth) corresponding thereto is calculated.

In order to simplify the descriptions here, propagation only from the sound source is assumed. In practice, however, the process includes forming the pseudo point reflection by transmission focusing. In this case, it is sufficient simply to add a transmission propagation duration to the above expression (2).

Herebelow, a method of finding the variation index in a case in which there is a non-uniform layer is described.

Figure 5:
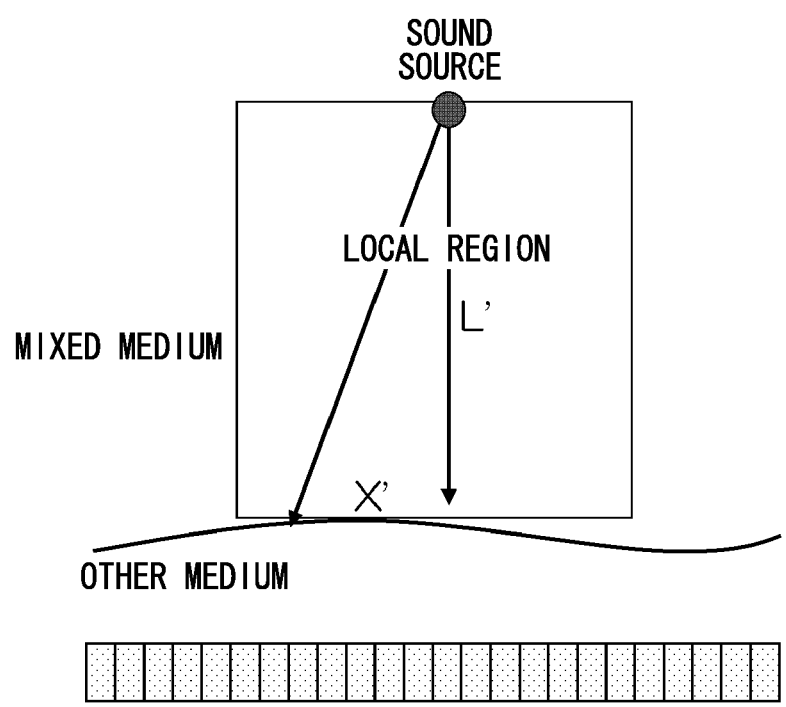
FIG. 5 is a drawing for explaining how the path length and average sound velocity are found when a distinct medium is present with the mixed medium.

In this case, as illustrated in FIG. 5, the variation index is calculated for a case in which a distinct medium that is different from the mixed medium is in front of the elements. More specifically, changes in the path lengths and reception timings are found by removing the effects of the distinct medium.

Firstly, in order to find the path lengths, as shown in FIG. 5, a local region is specified such that the vicinity of a boundary between the mixed medium and the distinct medium is at a lower face of the local region, and plural lattice points are specified along the lower face of the local region. When an average sound velocity in this region has been found, a depth L' of the sound source in the local region is found, and hence respective path lengths to the lattice points, which are separated by distances X', are found.

Various methods are available to find the average sound velocity in the local region (the local sound velocity), such as the technology described in JP-A No. 2010-99452 and the like, as described below.

For example, taking the sound source in FIG. 5 as a point of interest, first, an environmental sound velocity at the point of interest and the lattice points along the lower face of the local region is found. The term "environmental sound velocity value" is intended to include a sound velocity value at which the contrast and sharpness of an image are highest. An environmental sound velocity value may be found by the above-mentioned image analysis technique. Then, the waveform of a hypothetical reception wave $W_X$ if the point of interest acts as the reflection point is calculated on the basis of the environmental sound velocity value at the point of interest. An initial value of the assumed sound velocity in the local region is specified, and the assumed sound velocity is altered in single steps. A reception wave at the lattice points along the lower face of the local region is calculated from the environmental sound velocity, and a hypothetical compound reception wave $W_{SUM}$ in which the reception wave at the lattice points, with delays determined by the assumed sound velocity, are hypothetically combined is calculated.

Then, residuals (errors) between the hypothetical reception wave $W_X$ and the hypothetical compound reception wave $W_{SUM}$ are calculated. The residuals between the hypothetical reception wave $W_X$ and the hypothetical compound reception wave $W_{SUM}$ can be calculated by a method of finding a mutual cross-correlation, a method of applying delays obtained from the hypothetical compound reception wave $W_{SUM}$ to the hypothetical reception wave $W_X$ and performing phase matching addition, a method of conversely applying delays obtained from the hypothetical reception wave $W_X$ to the hypothetical compound reception wave $W_{SUM}$ and performing phase matching addition, or the like.

In order to obtain delays from the hypothetical reception wave $W_X$, it is sufficient to use the reflection point as the point of interest and use a time at which ultrasound propagated at the environmental sound velocity value from the point of interest reaches each element as the delay. In order to obtain delays from the hypothetical compound reception wave $W_{SUM}$, a line of equal phase is derived from phase differences between neighboring elements in the compound reception wave, and this line of equal phase may be used as the delays, or phase differences between maximum (peak) positions of the compound reception wave at the respective elements may be simply used as the delays. Further, cross-correlation peak positions of the compound reception wave from the respective elements may be used as the delays. Residuals at a time of phase matching addition may be found by a method of finding peak-to-peak values of the waveform after the matching addition, a method of finding maximum values of amplitude after envelope detection, and the like.

Then, after the calculation has been completed for all values of the assumed sound velocity, the local sound velocity value in the local region is determined. That is, the local sound velocity value in the local region is determined to be the value of the assumed sound velocity at which the differences between the hypothetical reception wave $W_X$ and the hypothetical compound reception wave $W_{SUM}$ are minimized.

The following is also available as a method that may measure the local sound velocity even in a case in which sound velocities in the imaging subject are non-uniform and the reception timings at the lattice points (the reception wave) cannot be approximated from the environmental sound velocity.

For example, a method is available of determining the local sound velocity by finding a point of interest within the region of interest and reception timings (reception waves) at the lattice points along the lower face of the local region in advance, superimposing lattice point reception waves with delays determined by an assumed sound velocity in the region of interest and combining the lattice point reception waves into a compound reception wave, and comparing this with the reception wave in the region of interest.

Alternatively, the local sound velocity may be determined by finding the point of interest within the region of interest and reception timings (reception waves) at the lattice points along the lower face of the local region in advance, then finding the sum of a propagation duration of ultrasound from the point of interest to each lattice point, which is determined by the assumed sound velocity in the region of interest, and the respective lattice point reception timing, using the smallest of these sums as a compound reception timing of the element and, for each element, comparing the reception timing of the ultrasound from the point of interest with the compound reception timing.

These reception timings at the point of interest and the lattice points along the lower face of the local region may be found using the above-mentioned image analysis technique and phase aberration analysis technique.

As an alternative method for finding the local sound velocity, for example, the reception timings (reception waves) at the lattice points along the lower face of the local region may be found by the image analysis and phase aberration analysis techniques in the same manner as described above. Then, the lattice point reception waves are superimposed with delays determined by the assumed sound velocity at the point of interest and combined into a compound reception wave, after which an image is generated on the basis of the generated delays, these images are analyzed, and the local sound velocity may be determined from, for example, a condition in which the sharpness is maximized.

Or, after the reception timings (reception waves) at the lattice points have been found, the sum of a propagation duration of ultrasound from the point of interest to each lattice point according to the assumed sound velocity in the region of interest and the respective lattice point reception timing may be found, the smallest of these sums may be used as a delay of the element, and an image may be generated on the basis of these delays. These images are analyzed and the local sound velocity may be determined from, for example, a condition in which the sharpness is maximized.

As a further alternative, the reception timings (reception waves) at the lattice points along the lower face of the local region may be found by image analysis and phase aberration analysis techniques in the same manner as described above. These reception timings may be used as delays, and the lattice points along the lower face of the local region may be treated as hypothetical elements. As reception signals of the hypothetical elements, signals for which matching addition with the delays has been performed may be specified, and an image may be generated from the reception signals at the hypothetical elements on the basis of the assumed sound velocity at the point of interest. These images are analyzed, and the local sound velocity may be determined from, for example, a condition in which the sharpness is maximized.

The methods for specifying the above lattice points and the lower face of the local region are not particularly limited to a flat surface. An arbitrary curved surface at the element side (the near side to the elements) relative to the point of interest may be specified. For example, a surface of a boundary of a tissue, a lesion or the like may be specified.

Next, as a method of finding changes of the element reception timings, changes in the reception timings of the signals received at the elements are found from reception timings determined in accordance with the average sound velocity. Changes caused by the distinct medium are removed from these changes by applying filter processing to cut low frequencies, and the element positions are converted to the lattice point positions at the lower face of the local region. For the conversion from the element positions to the lattice point positions at the lower face of the local region, ultrasound propagation paths from the point of interest through the lattice points to the elements are calculated from the local sound velocity in the local region and the environmental sound velocities or the element reception timings at the lattice points. Hence, the conversion may be performed by propagating in the reverse direction along the propagation paths from the element positions.

The changes found in this manner are divided by the propagation lengths, providing the indices obtained from the above expression (1), and the standard deviation thereof may be used as the variation index.

Now, a method of finding attenuation variations is described.

As described below, the attenuation variations may be found by a method similar to that for the sound velocities, using amplitudes or central frequencies instead of reception timings of the reception signals.

There are three kinds of attenuation: diffusion attenuation, caused by the spreading of ultrasonic waves; absorption attenuation, caused by ultrasonic waves being absorbed by a medium and converted to heat; and scattering attenuation, caused by scattering in organic tissues. Of these, absorption and scattering attenuation are given by exp(−αx), in which α represents an attenuation coefficient and x represents a propagation distance.

According to "Cho'onpa Binran" (Ultrasound handbook), published by Maruzen, 1999, in organic tissues it may be assumed that the attenuation coefficient α in a frequency range in the megahertz band is approximately proportional to frequency. Due to the attenuation being proportional to frequency, the central frequency of a Gaussian pulse shifts in proportion to a propagation distance. Utilizing this fact, attenuation may be found from a central frequency shift.

Now, the variation index for attenuation is considered in the same manner as in the case of sound velocity.

After logarithmic compression of respective paths from a sound source, amplitude $A(x)$ and a central frequency $F(x)$ are given by the following expression (4).

$$A(x)=A(0)-L\times(\alpha 1\times\rho 1+\alpha 2\times\rho 2)-L\times\Delta\rho\times(\alpha 1-\alpha 2)$$

$$F(x)=F(0)-L\times(\beta 1\times\rho 1+\beta 2\times\rho 2)-L\times\Delta\rho\times(\beta 1-\beta 2) \quad (4)$$

This expression disregards the effects of diffusion, transmission focusing, non-linearity, directionality and the like on the amplitude. In this expression, α represents an attenuation coefficient, including an element dependent on frequency, and β represents a constant determined by α and the bandwidth of a pulse wave (a Gaussian pulse is assumed).

From the above expression (4), an amplitude and central frequency that do not take account of path variations are given by the following expression (5).

$$A(x)=A(0)-L\times(\alpha 1\times\rho 1+\alpha 2\times\rho 2)$$

$$F(x)=F(0)-L\times(\beta 1\times\rho 1+\beta 2\times\rho 2) \quad (5)$$

The following expression (6) is obtained by subtracting expression (5) from the above expression (4), and dividing a change in the amplitude that is found ($L\times\Delta\rho\times(\alpha 1-\alpha 2)$), or a change in the frequency that is found ($L\times\Delta\rho\times(\beta 1-\beta 2)$), by the path length L.

$$\Delta\rho\times(\alpha 1-\alpha 2) \text{ or } \Delta\rho\times(\beta 1-\beta 2) \quad (6)$$

Thus, an index that is independent of the path length is obtained.

The path length L in this case can be found from the average sound velocity by, for example, the above expression (3). Amplitudes or central frequencies that are independent of the paths are required to obtain the change amounts, and these may be found by fitting the element reception signals to amplitudes or central frequencies. Average values of α or β may be assumed on the basis of the depth of the sound source found from expression (3) and may be used for the fitting.

If transmission paths are also to be considered, it is sufficient to append the following expression to expression (4).

$$-(\text{transmission path length})\times(\alpha 1\times\rho 1+\alpha 2\times\rho 2)$$

As a method for finding the variation index in a case in which a non-uniform layer is present, it is sufficient to find path lengths in a local region in FIG. 5, and find changes represented by the above expression (6) from the average attenuation of amplitudes or central frequencies at the lattice points along the lower face of the local region. The path lengths may be found together with the average sound velocity of the local region.

Examples of methods to find sound velocity variations and attenuation variations are illustrated hereabove, but numerous variants of these methods are available.

Figure 6:
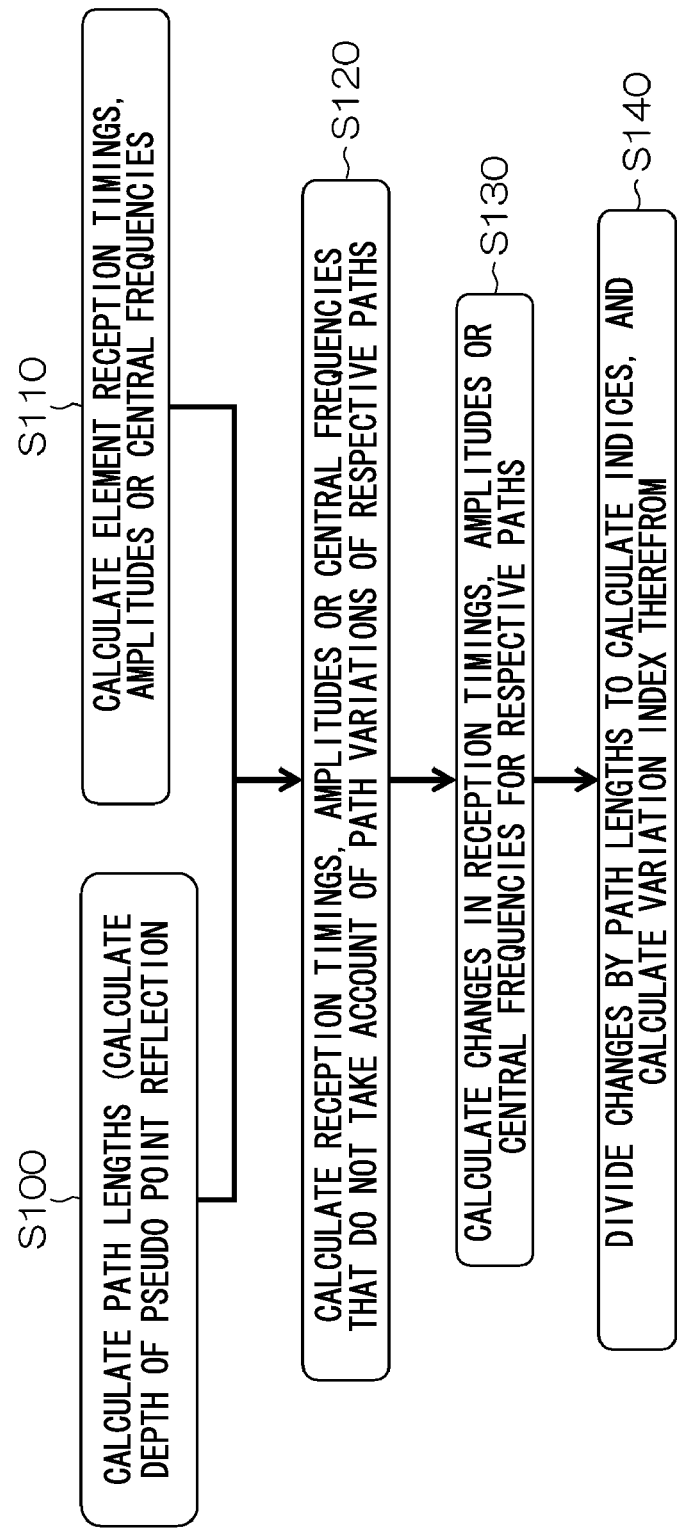
FIG. 6 is a flowchart showing how sound velocity variations and attenuation variations are calculated when there is no distinct medium.
Figure 7:
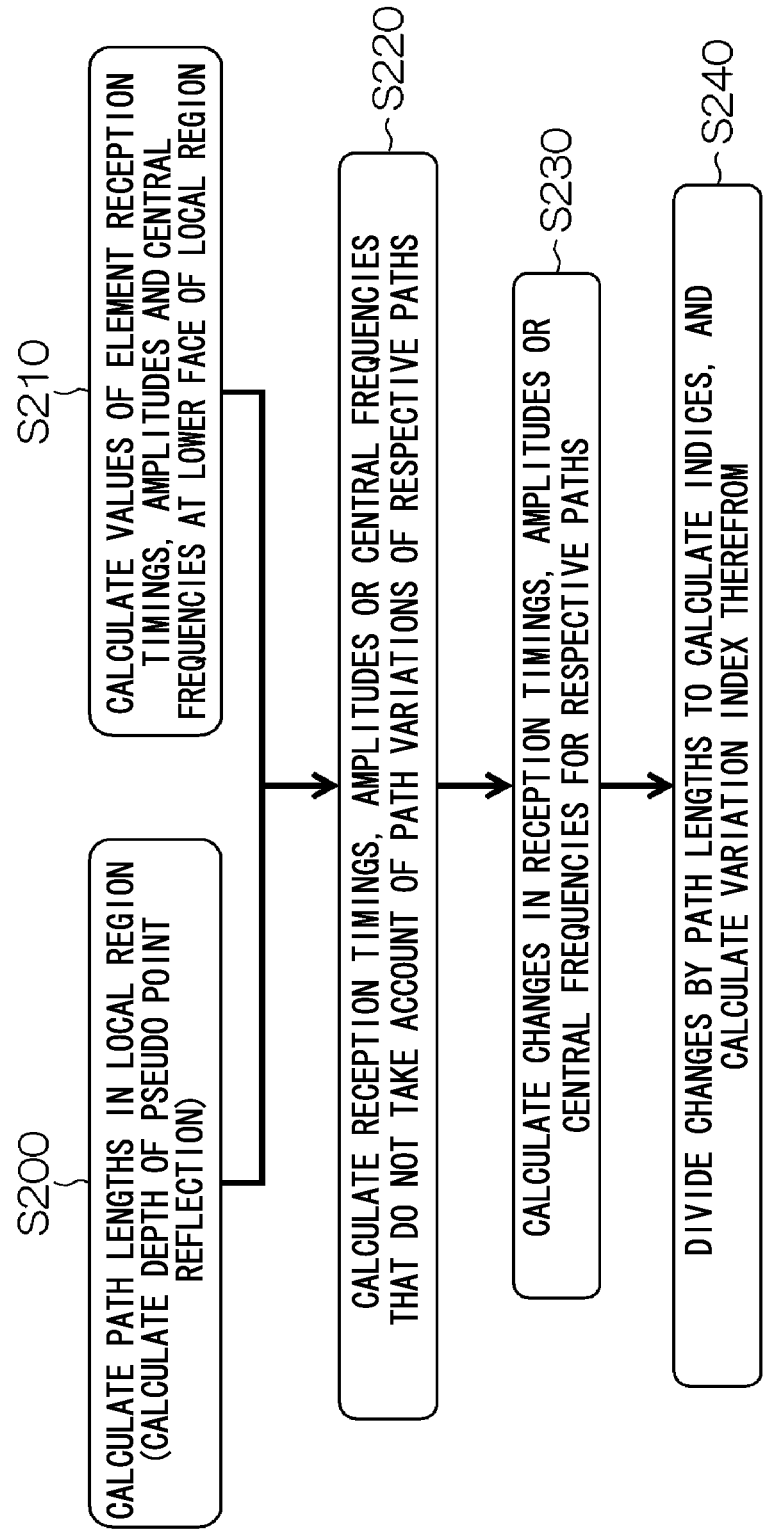
FIG. 7 is a flowchart showing how sound velocity variations and attenuation variations are found when a distinct medium is present.

FIG. 6 and FIG. 7 show methods of finding a variation index (for sound velocity variations or attenuation variations), divided into steps and summarized. FIG. 6 illustrates a case in which there is no distinct medium, and FIG. 7 illustrates a case in which a distinct medium is present.

First, the method of finding a variation index in a case in which there is no distinct medium is described with reference to the flowchart in FIG. 6.

In step S100, path lengths are calculated. Path lengths linking the point of interest with the elements may be calculated by calculating the depth of a point of interest (a sound source).

As a method for calculating the depth of a point of interest, there are methods such as, for example, a method of finding the depth from reception timings, a method of finding the depth from amplitudes, a method of utilizing central frequencies, and the like.

As a method for finding the depth from reception timings, for example, the average sound velocity and depth as far as the point of interest may be found using a known image analysis technique. To be specific, the average sound velocity and depth may be found in the form of values at which a characteristic such as the sharpness or contrast of an image of the point of interest is maximized.

As a method for finding the depth from amplitudes, for example, a method may be considered of acquiring amplitudes of the element reception signals, fitting the amplitudes to amplitudes found by assuming the average sound velocity and depth as far as the point of interest in the above expression (5), and employing the values at which residuals are minimized. However, because amplitudes are affected not just by attenuation but also by diffusion, transmission focusing, non-linearity and the like, applying expression (5) is difficult. In this regard, a method that utilizes amplitude ratios of two frequencies, for example, the method disclosed in Japanese Patent Application Publication (JP-B) No. H3-24868, may be used, and the depth may be found using the fact that the difference between logarithmically compressed amplitudes of two frequencies being proportional to an attenuation coefficient.

As a method that utilizes central frequencies, a method may be considered of acquiring central frequencies of the element reception signals, fitting these central frequencies to central frequencies found by assuming the average sound velocity and depth as far as the point of interest in expression (5), and employing the values at which residuals are minimized. In this case, the fitting may be performed more accurately if the central frequency when the waves are transmitted is known.

In step S110, element reception timings, amplitudes or central frequencies are calculated.

The reception timings may be found using a known phase aberration analysis technique, as described above. The phase aberration analysis may be performed using reception timings that do not take account of path variations, which have found in advance together with an average sound velocity from image analysis of the point of interest, as reference points.

The amplitudes may be found using a method of applying envelope detection to the element reception signals, converting the results to amplitude information, and then acquiring values at the reception timings mentioned above. A peak value in a predetermined range may be acquired using the reception timings that do not take account of path variations as reference points.

The central frequencies may be found using a method of acquiring a predetermined range from the element reception signals, using the reception timings mentioned above as reference points, converting the frequencies, and then finding a center of gravity from the expression $\int f \times P(f) \cdot df / \int P(f) \cdot df$. In this expression, f represents frequency and P(f) represents the spectral density at f. A central frequency may be a frequency at which the spectral density peaks, or may be the middle of a half-amplitude width. The central frequency may also be found from slopes in the depth direction of phases obtained by applying wave detection processing.

In the above descriptions, when finding an amplitude or central frequency, noise and interference may be reduced by matching addition of signals at corresponding reception timings in a predetermined aperture that is centered on the reception signal of the element being found.

Then, in step S120, reception timings, amplitudes and central frequencies of the respective paths that do not take account of path variations are calculated.

The reception timings may be found using the average sound velocity found in the above-mentioned step S100. Alternatively, the reception timings may be found by fitting a curve that minimizes residuals to the element reception signals found in step S110. Here, because the path lengths linking the point of interest with the elements have been found in step S100, an average sound velocity may be assumed to calculate the reception timings, and an average sound velocity (and hence reception timings) that minimizes residuals may be found.

The amplitudes may be found by fitting a curve that minimizes residuals to the amplitudes of the element reception signals found in step S110. Here, because the path lengths linking the point of interest with the elements have been found in step S100, amplitudes may be calculated while assuming the average attenuation in expression (5), and an average attenuation (and hence amplitudes) that minimizes residuals may be found.

Regarding the central frequencies, if the average attenuation has been found in step S100, the central frequencies at the elements are found at the same time. Alternatively, the central frequencies may be found by fitting a curve that minimizes residuals to the central frequencies of the element reception signals found in step S110. Here, because the path lengths have been found in step S100, the central frequencies may be calculated while assuming the average attenuation, and an average attenuation (and hence central frequencies) that minimizes residuals may be found. In this case, the fitting may be performed more accurately if the central frequency when the ultrasound is transmitted is known.

Then, in step S130, changes in the reception timings, amplitudes or central frequencies of the respective paths are calculated. These may be found by subtracting the values found in step S120 from the reception timings, amplitudes or central frequencies found in step S110.

Then, in step S140, the changes are divided by the path lengths to calculate indices, and the variation index is calculated from these indices. The variation index may be a standard deviation, a maximum value or the like of the respective path indices.

Next, the method of finding a variation index when a distinct medium is present is described with reference to the flowchart in FIG. 7.

The flowchart in FIG. 7 is substantially the same as the flowchart of FIG. 6 described above, but differs in that, in the method of calculating the variation index at the point of interest, "paths" is replaced with "paths in the local region", and "element reception timings, amplitudes or central frequencies" are replaced with "values along the lower face of the local region".

First, in step S200, path lengths in the local region are calculated (i.e., the depth of the pseudo point reflection is calculated). For example, as shown in FIG. 5, a local region is specified with points of interest (sound sources) along the upper face and the vicinity of the boundary with the distinct medium as the lower face, and path lengths within the local region are found. Firstly, the depth of a point of interest in the local region is found. A method of finding the depth together with the average sound velocity in the local region may be suitably used as a method for finding the depth. Various methods as described above are available as methods for finding the average sound velocity in the local region (the local sound velocity).

In step S210, values for element reception timings, amplitudes or central frequencies at the lower face of the local region are calculated.

As a method for finding local reception timings in the local region, known image analysis and phase aberration analysis techniques may be used to find the reception timings (and the average sound velocity) at the lattice points along the lower face of the local region, and these are used as delays. A reception timing (reception wave) at the point of interest is found by image analysis and phase aberration analysis. The lattice points are treated as hypothetical elements, and signals for which matching addition of the reception wave at the point of interest with the delays has been performed are specified as reception signals of the hypothetical elements. A local reception timing at the point of interest is found by applying phase aberration analysis to reception signals at the hypothetical elements. Alternatively, with the lattice points being treated as hypothetical elements, a latest timing among timings for which the delays are subtracted from the element reception timings at the point of interest is employed as a local reception timing of the hypothetical elements.

Or, reception waves at the lattice points along the lower face of the local region are all regarded as being the same, a representative reception wave is specified, and the local reception timing at the point of interest is found by applying deconvolution with the reception wave representing the lattice points along the lower face of the local region to the reception wave at the point of interest. The deconvolution processing may be applied to the element reception signals or in a frequency space thereof.

Or, the local reception timings may be found such that residuals between the reception timings (reception waves) at the point of interest, and the reception timing (reception wave) at the point of interest, which is found from the reception timings (reception waves) at the lattice points along the lower face of the local region and propagation durations from the point of interest to the lattice points (local reception timings), are minimized. Various algorithms may be used as a minimum value search algorithm. For example, a quasi-Newton method may be used.

As a method for finding the central frequencies, local reception timings in the local region or the average sound velocity, and reception timings at the lattice points along the lower face of the local region or the average sound velocity are found in advance. Hence, a propagation path from the point of interest→each lattice point→the respective element is calculated. It is assumed that the central frequency when the ultrasound is transmitted is already known.

Central frequency shift amounts from the lattice points along the lower face of the local region to (→) the respective elements are found by the following procedure.

First, the central frequencies are found from the element reception signals at the lattice points (here, noise and interference may be reduced by matching addition of signals at corresponding reception timings in a predetermined aperture that is centered on the reception signal of the element to be found). The central frequency shift in one direction for a particular lattice point is a value represented by the expression below.

(central frequency [reception signal at middle element])−(central frequency [at transmission])/2

A value obtained by subtracting this value from (central frequency [reception signal at middle element])−(central frequency [at transmission]), represents a central frequency shift that is caused by attenuation along the propagation path from the lattice point to the element.

Even if the central frequency when the ultrasound is transmitted is unknown, if uniform attenuation along the whole path from the lattice point to the element is assumed, the attenuation coefficient can be found and the shift amount can be found therefrom (however, accuracy is better if the central frequency when the ultrasound is transmitted is known).

The central frequency shift from each lattice point to the respective element is subtracted from the central frequency at the element for the point of interest, to find the central frequency at the lattice point.

As a method for finding the amplitudes, attenuations from the lattice points to the elements are found in advance from the frequency shift amounts, and the propagation paths from the lattice points to the elements are found. The amplitudes at the elements are corrected with the attenuations from the lattice points to the elements, to find the amplitudes at the lattice points.

Then, in step S220, reception timings, amplitudes or central frequencies that do not take account of path variations in the local region are calculated.

The reception timings may be found from the average sound velocity and path lengths in the local region that have been found in step S200. Alternatively, a curve that minimizes residuals may be fitted to the lattice point reception timings found in step S210 to find the reception timings. Here, because the path lengths linking the point of interest with the lattice points have been found in step S200, an average sound velocity may be assumed to calculate the reception timings, and an average sound velocity (and hence reception timings) that minimizes residuals may be found.

The amplitudes may be found by fitting a curve that minimizes residuals to the amplitudes at the lattice points found in step S210. Here, because the path lengths linking the point of interest with the lattice points have been found in step S200, the average attenuation in expression (5) may be assumed to calculate amplitudes, and an average attenuation (and hence amplitudes) that minimizes residuals may be found.

The central frequencies may be found by fitting a curve that minimizes residuals to the central frequencies at the lattice points found in step S210. Here, because the path lengths have been found in step S200, the average attenuation may be assumed to calculate central frequencies, and an average attenuation (and hence central frequencies) that minimizes residuals may be found.

The processing of steps S230 and S240 is the same as the above-described processing of steps S130 and S140 in FIG. 6 for the case in which there is no distinct medium, so the description thereof is omitted.

Herein, the lower face of the local region that is specified in a case in which a distinct medium is present need not necessarily be in the vicinity of the boundary as shown in FIG. 5, and may be a curved surface rather than a flat surface. In order to find the reception timings, amplitudes and central frequencies of the lattice points along the lower face of the local region, a transmission focusing point may also be specified at the lower face of the local region, as well as for the local region.

A method is also available for finding the changes in the reception timings, amplitudes or central frequencies at the lattice points by removing the changes caused by the distinct medium, by applying filter processing to cut low frequencies from the reception timings, amplitudes or central frequencies of the signals received at the respective elements, and converting the element positions to lattice point positions along the propagation paths from the lattice points to the elements.

Note that correction for a distinct medium, normalization by path length and the like are not necessarily required. However, it is desirable that a ratio between the depth and the aperture of the elements is constant.

In a case of performing normalization, alternatively to the path length, the depth or a quantity similar to the depth may serve as a normalization quantity. A quantity similar to the depth may be a reception timing or frequency shift amount at the middle element (or lattice point), or the like. Normalization by these quantities is not necessary in a case of evaluating variations when the depths of points of interest (regions of interest) are constant (depths excluding the distinct medium if there is a distinct medium).

From the above expression (3) and the like, it can be seen that the sound velocity and attenuation are quantities that are dependent only on $\Delta\rho$, unrelated to the depth. Therefore, sound velocities or attenuations may serve as variation indices (in which case it is likely that the ratio between the depth and the aperture is irrelevant).

The variation index in that case may be: a sound velocity or attenuation range in which averages of absolute values or squares of differences from an approximation curve of sound velocities or attenuations are within a predetermined ratio of a minimum value; or a sound velocity or attenuation range at both sides adjacent to a measured reception timing, amplitude or central frequency. In the case of sound velocities, the variation index may be a sound velocity range in which focusing indices of images subjected to matching addition have predetermined ratios to the maximum, or a standard deviation of sound velocities or attenuations that are found by dividing the aperture into small apertures and finding the sound velocities or attenuations in the small apertures, or the like may be used.

When including variations of ultrasonic wave propagation durations, amplitude changes, and central frequency shifts along transmission paths, the average sound velocity and the average attenuation themselves may vary depending on the position of the point of interest. Therefore, the standard deviation of variations in the average sound velocity or average attenuation at points of interest in the region of interest may serve as the variation index.

Now, variation indices based on spatial frequency are described.

The variation index described above is an index based on the amounts of variations in reception timings, amplitudes or central frequencies. However, altering variations in spatial frequency can also be considered. More specifically, the frequency with respect to directional position of the changes in reception timing, amplitude or central frequency illustrated in FIG. 2A to FIG. 2C may vary, and consequently a variation index may be based thereon.

Changes in the reception timings, amplitudes and central frequencies can be obtained by the flowchart of FIG. 6 in a case in which there is no distinct medium, and by the flowchart in FIG. 7 in a case in which a distinct medium is present.

The amounts of changes in the reception timings, amplitudes and central frequencies increase with the depth of the point of interest, but there is no need for correction if the amounts of changes at respective directional positions increase uniformly because this does not affect the frequency. However, since there are slight differences in how the changes increase depending on paths, the changes may be corrected by normalization by path lengths. That is, either of the changes provided by the flowcharts of FIG. 6 and FIG. 7 or these changes normalized by path lengths may be used as variation indices.

In this case, even if the depth of points of interest is not constant, there is no need to correct the frequencies of changes with respect to directional positions in accordance with depths, path lengths or the like. However, it is preferable to perform evaluation with a constant aperture.

A central frequency or bandwidth of a frequency distribution with respect to directional positions of the indices obtained as described above, or a variable based thereon, is found to serve as the variation index.

For example, in the case of cirrhosis, because hepatic lobules that are uniform and small are replaced with nodules that are non-uniform and large, a central frequency may move to the low-frequency side or the bandwidth may widen. Therefore, a level of cirrhosis may be diagnosed from this variation index.

The central frequency can be found from $\int f \times P(f) \cdot df / \int P(f) \cdot df$, in which f represents frequency and P(f) represents the amplitude at f. The central frequency may also be a frequency at which the amplitude is at a maximum, may be the central frequency of a band in which amplitudes have a predetermined ratio to the maximum amplitude, or may be the frequency at which the integrated value of P(f) is at a half-value.

The bandwidth can also be found from the square root of $\int (f-f_0)^2 \times P(f) \cdot df / \int P(f) \cdot df = \int f^2 \times P(f) \cdot df / \int P(f) \cdot df - f_0^2$, in which $f_0$ represents the central frequency. This may simply be a variance. Alternatively, a bandwidth in which amplitudes have a predetermined ratio to the amplitude of the central frequency, the maximum amplitude, or the like may be used as the bandwidth. A bandwidth in which the integral P(f) is a predetermined ratio of the total integral value around the central frequency, the frequency of the maximum amplitude or the like may also be used as the bandwidth.

Beside the central frequency and the bandwidth, a skew of a frequency distribution may be found to serve as the variation index. This can be calculated from a three-dimensional moment of the frequency distribution $\int (f-f_0)^3 \times P(f) \cdot df / \int P(f) \cdot df$.

Hereabove, methods are described in which changes in the reception timings, amplitudes and central frequencies, changes in normalized path lengths and the like serve as indices for finding the variation index. However, rather than the changes, the reception timings, amplitudes and central frequencies may be directly used as the indices. In this case, because a component of the reception timings, amplitudes or central frequencies that do not take account of path variations is included in the lowest frequencies of the frequency distribution, the lowest frequency components may be removed when calculating the variation index.

The variation index may also be found on the basis of a spatial frequency of variations with point of interest positions in the average sound velocity or average attenuation. In this case, a two-dimensional frequency distribution of average sound velocities or average attenuations in a region of interest may be found, and the variation index may be calculated from the central frequency, bandwidth or skew of the two-dimensional frequency distribution.

In the present exemplary embodiment, the variation index may be found as described above. However, it is likely that the effects of non-uniformity of micro-structures on variations in signals vary depending on a relationship between the scale of micro-structures and wavelengths (frequencies). For example, if a wavelength is significantly longer than the structures (if the frequency is significantly low), non-uniformity of the structures has virtually no effect on signal variations. Conversely, if the wavelength is broadly similar to the scale of the structures, non-uniformity of the structures is likely to have a great effect. Specifically, in the case of a fatty liver, since the fat droplet size is around 100 μm, it is contemplated that non-uniformity due to fat deposition can be captured at a frequency of around 7 MHz.

Therefore, in the present embodiment, at the time of measuring the variations index and carrying out diagnosis of tissue characteristics, ultrasonic waves are transmitted at a predetermined transmission frequency that is suited to diagnosis of tissue characteristics. Specifically, in the present embodiment, the transmission frequency for B-mode, and the transmission frequency for tissue characteristic diagnosis, are switched to different frequencies. The transmission frequency for B-mode is made to be a predetermined frequency, and the transmission frequency for tissue characteristic diagnosis is made to be a frequency that is predetermined in accordance with the depth and size of the region of interest (the organ of interest or lesion).

Figure 8:
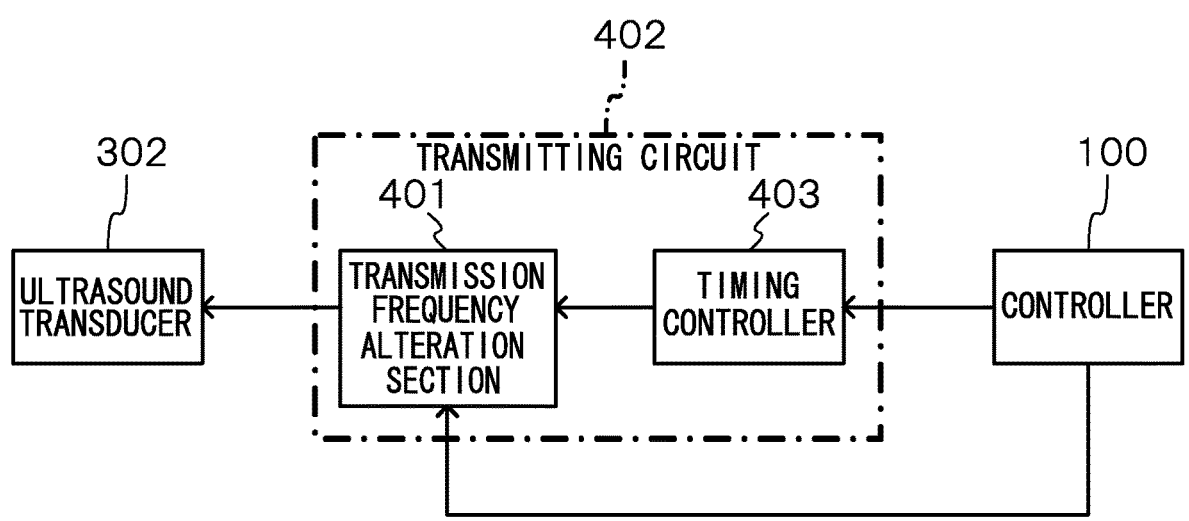
FIG. 8 is a drawing showing an example of a transmittion circuit that can change the transmission frequency of the ultrasound diagnostic device relating to the exemplary first embodiment.

FIG. 8 is a drawing showing an example of a transmission circuit that can change the transmission frequency of the ultrasound diagnostic device 10 relating to the exemplary first embodiment.

Figure 9:
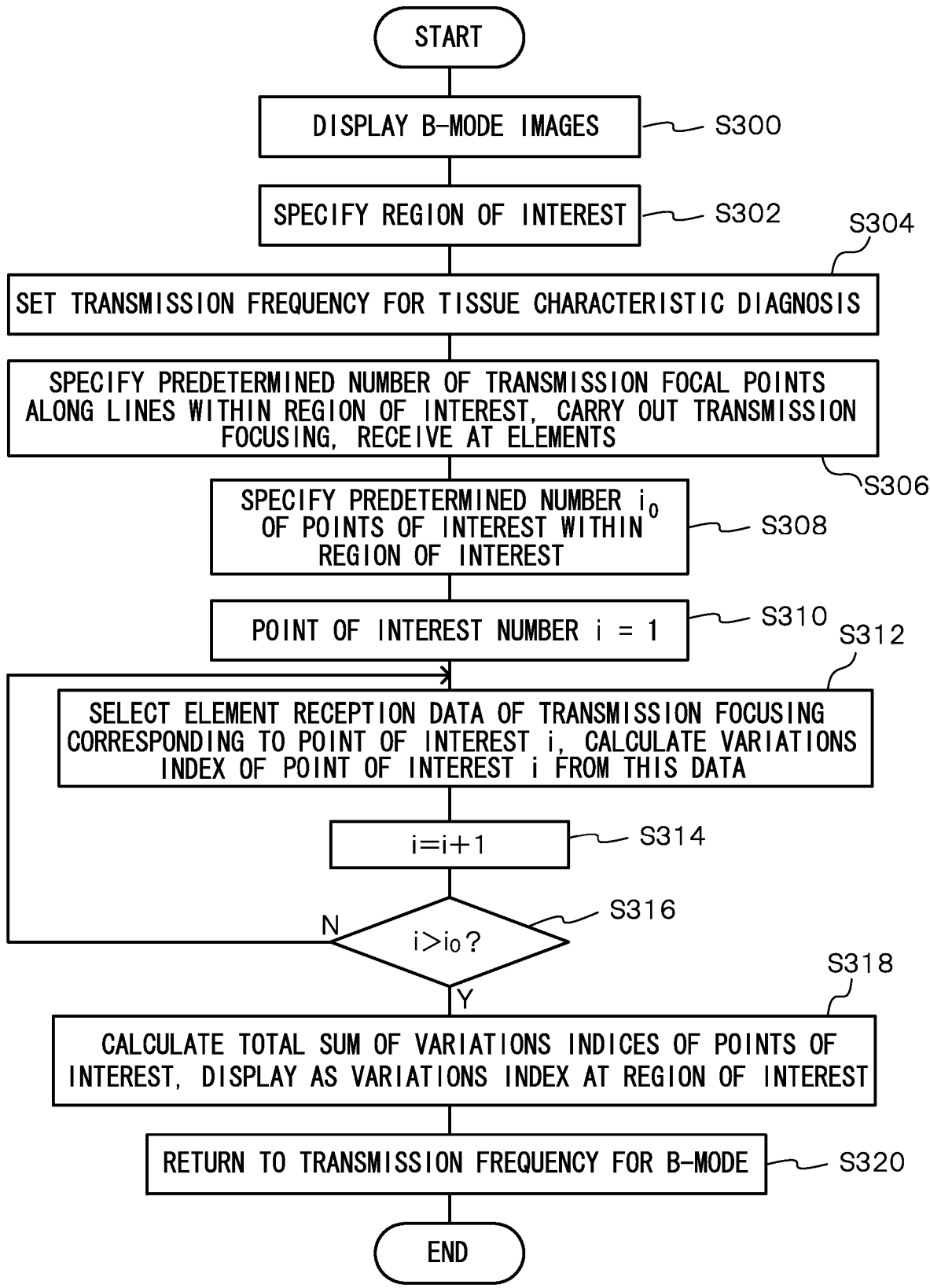
FIG. 9 is a flowchart showing an example of an overall flow of processing to calculate a variation index representing sound velocity variations or attenuation variations, which is executed by a controller of the ultrasound diagnostic device of the first exemplary embodiment.

In the present exemplary embodiment, as shown in FIG. 9, the transmission circuit 402 includes a transmission frequency alteration section 401 and a timing controller 403.

The timing controller 403 outputs signals to the transmission frequency alteration section 401 to generate driving pulses under the control of the controller 100.

The transmission frequency alteration section 401 generates pulses at frequencies according to instructions from the controller 100 and outputs the pulses to the ultrasound transducers 302. Hence, ultrasonic waves at frequencies according to the instructions from the controller 100 are produced from the ultrasound transducers 302. As a method for altering the transmission frequency from the transmission frequency alteration section 401, for example, the technology recited in JP-A No. 2006-255014 or the like may be employed. More specifically, the ultrasound transducers 302 with a wide-band frequency characteristic that employ compound-type piezoelectric elements are employed, plural bandpass filters that pass different frequency bands are connected to the ultrasound transducers 302, and the driving pulses are selectively applied, while switching between the bandpass filters. Thus, ultrasonic waves with different frequency bandwidths and central frequencies may be produced. Alternatively, plural types of the ultrasound transducers 302 with different frequency characteristics may be provided and selectively used.

Now, operations of the ultrasound diagnostic device 10 according to the first exemplary embodiment of the structure described above are described.

FIG. 9 is a flowchart showing an example of the overall flow of processing to calculate a variation index representing sound velocity variations or attenuation variations, which is executed by the controller 100 of the ultrasound diagnostic device 10 in accordance with the first exemplary embodiment.

First, in step S300, a B-mode image is displayed. That is, a B-mode image is displayed at the display unit 104 in response to operation of the display mode switching button of the console 202 by a user. While the B-mode image is being displayed, the controller 100 controls the transmission frequency alteration section 401 of the transmission circuit 402 such that the transmission frequency is a B-mode frequency, and receives ultrasound signals from the ultrasound probe 300.

Then, in step S302, a region of interest is specified. For example, a region being specified in accordance with operations of the console 202 or the pointing device 204 by the user may be specified as the region of interest.

Next, in step S304, the transmission frequency is set to the transmission frequency for tissue characteristic diagnosis. For the transmission frequency for tissue characteristic diagnosis, for example, a frequency that is different than that for B-mode images and that is suited for diagnosing tissue characteristics is set in advance. The controller 100 controls the transmission frequency alteration section 401 such that the transmission frequency is changed.

In step S306, the transmission circuit 402 controls the ultrasound transducers in response to instructions from the controller 100, specifies a predetermined number of transmission focusing points along respective lines in the region of interest, and applies corresponding transmission focusing, and the reception circuit 404 receives signals via the respective elements. The RF signals received by the reception circuit 404 are converted to digital RF signals by the A/D converter 406.

In order to select transmission focusing that corresponds to each point of interest at this time, the effective region of each transmission focusing may be determined in advance as follows.

First, a transmission focus identification number (n) is specified, a designated line width for a predetermined designated line number is added or subtracted to set a line number (m), and element reception signals for focusing point (n) and line (m) are read out. Then, a specified sound velocity number (k) is specified, reception focusing for the specified sound velocity (k) is applied to received signals from line (m) of transmission focus (n), and an index or image is saved. This processing is repeated for different values of the specified sound velocity (k), and after the processing has been completed for predetermined specified sound velocities, line (m) is altered and, as above, the transmission focusing is applied with the different specified sound velocities (k) to the new line (m).

Next, an environmental sound velocity (average sound velocity) is found for each depth from the indices or images of all lines at the respective specified sound velocities. A standard deviation of the environmental sound velocities in the depth direction is calculated, a minimum point is determined to be the actual focusing point depth, and an effective area for the transmission focus (n) is found. Then the transmission focus identification number is altered, and an effective area is found for the next transmission focus (n) in the same manner as described above.

The transmission focusing may be performed corresponding to each point of interest.

In step S308, the data analysis and measurement section 106 specifies a predetermined number ($i_0$) of points of interest in the region of interest for the RF signals. There may be a single point of interest; that is, the predetermined number $i_0$ may be 1. By the processing described below, a variation index representing sound velocity variations or attenuation variations at the point of interest is found for each of the $i_0$ points of interest.

Firstly, in step S310, of the predetermined number ($i_0$) of points of interest in the region of interest for the RF signals, the data analysis and measurement section 106 sets a value i representing an identification number (No.) of a point of interest to 1 (i=1).

In step S312, element reception data for a transmission focus corresponding to the point of interest with identification number i is selected, and the variation index representing sound velocity variations or attenuation variations for the point of interest with identification number i is calculated from this data. In a case in which there is no distinct medium, the method for finding the variation index is the above-described method illustrated in the flowchart of FIG. 6, and in a case in which a distinct medium is present, the method for finding the variation index is the above-described method illustrated in the flowchart of FIG. 7. At this time, a local region is specified distinctly from the region of interest, and the element reception data of transmission focusing corresponding to lattice points along the lower face of the local region is also used.

In step S314, the data analysis and measurement section 106 increments the point of interest identification number i by 1 (1 is added to i). In step S316, a determination is made as to whether i exceeds the specified number of points of interest (the predetermined number $i_0$). If the result of this determination is that i has not exceeded $i_0$, the controller 100 returns to step S312 and repeats the above-described processing to find a variation index representing sound velocity variations or attenuation variations at this point of interest i. If it is determined that i is above $i_0$, the controller 100 proceeds on to step S318.

In step S318, the data analysis and measurement section 106 calculates the sum of the variation indices for the respective points of interest i, and displays this sum on the display unit 104 as a variation index of the region of interest.

In the present exemplary embodiment, the sum of the variation indices of the respective points of interest is used as the variation index of the region of interest. However, instead of using the sum, after finding the variation indices of all of the points of interest, a standard deviation thereof may be calculated and used as the variation index of the region of interest.

Next, in step S320, the transmission frequency is returned to the transmission frequency for B-mode. Namely, the controller 100 controls the transmission frequency alteration section 401 to change the transmission frequency to the transmission frequency for B-mode that is predetermined, and the series of processings for determining the variations index for tissue characteristic diagnosis is ended.

Hereabove, a variety of sound velocity and attenuation variation indices based on changes in reception timings, amplitudes and central frequencies, and a variety of variation indices based on changes in average sound velocity and average attenuation in accordance with positions of points of interest have been described. However, embodiments are not limited to the examples described above, and it will be clear that numerous alternative variation indices may be used within a scope not departing from the spirit of the invention. For example, after finding indices based on reception timings, amplitudes or central frequencies at all of the points of interest in the region of interest, a characteristic quantity of the shape of a histogram thereof—skew, kurtosis or the like—may be used as the variation index. Or, indices for respective points of interest may be averaged and then a standard deviation of a distribution in the region of interest, a characteristic quantity of the shape of a histogram, or a characteristic quantity of texture according to a concurrent matrix or the like—for example, uniformity, contrast, correlation, entropy or the like—may be used as the variation index.

Similarly, a characteristic quantity of a histogram, a characteristic quantity of texture or the like based on a distribution in the region of interest of average sound velocities or average attenuations may be used as the variation index. Or, rather than using a single such characteristic quantity as a variation index, for example, multiple regression from a plural number of characteristic quantities may be found for a variation index.

Thus, an index that represents variations in sound velocity or attenuation (the variation index) may be calculated, and this index may be used to diagnose a tissue characteristic.

For example, concrete data of lesions and of variations in sound velocity or attenuation that correspond thereto may be gathered in large quantities, statistical correspondences between variation index values and tissue characteristic states may be found on the basis of this data, and variation index thresholds for diagnosing tissue characteristics may be specified in advance. Then, in an actual diagnosis, a variation index may be found by the method described above and this variation index may be compared with the pre-specified thresholds to perform diagnosis of the tissue characteristic. As a result, diagnosis of the tissue characteristic may become simple.

Moreover, since diagnosis is carried out by changing the transmission frequency to a frequency that is suited to the diagnosing of tissue characteristics, non-uniformity of micro-structures can be measured highly accurately. For example, in the case of a fatty liver, because the fat droplet size is around 100 μm as described above, by changing the transmission frequency to around 7 MHz, non-uniformity due to fat deposition can be captured with high accuracy as compared with a case in which the frequency is not changed.

Second Embodiment

In the first exemplary embodiment, micro-structural non-uniformity of sound velocity or attenuation in a tissue is measured on the basis of variations in the times, amplitudes, frequencies or the like of respective element signals. In the second exemplary embodiment, a sound velocity or attenuation is found on the basis of element signals, and micro-structural non-uniformity of sound velocity or attenuation in a tissue is measured on the basis of spatial variations of the sound velocity or attenuation. The structure of the second exemplary embodiment is the same as the ultrasound diagnostic device 10 according to the first exemplary embodiment but the processing carried out by the controller 100 is different, so only the processing that differs is described below.

Figure 10:
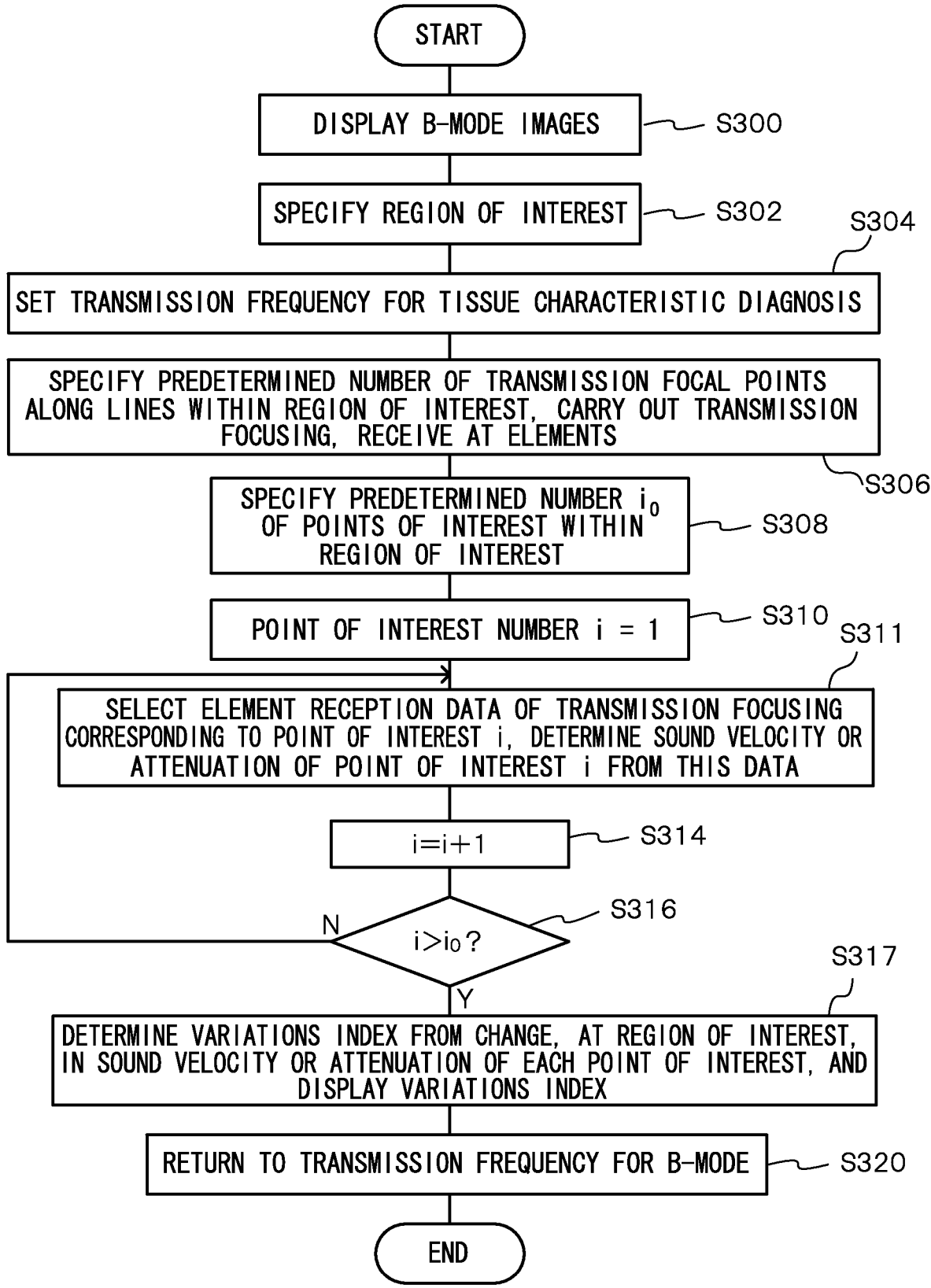
FIG. 10 is a flowchart showing an example of a flow of processing to calculate a variation index of sound velocity or attenuation, which is executed by a controller of an ultrasound diagnostic device of a second exemplary embodiment.

FIG. 10 is a flowchart showing an example of the overall flow of processing to calculate a variation index representing sound velocity or attenuation variations, which is executed by the controller of the ultrasound diagnostic device in accordance with the second exemplary embodiment. Processing that is the same as in the first exemplary embodiment is assigned the same reference numerals in FIG. 11 and is only briefly described.

First, in step S300, a B-mode image is displayed. Then, in step S302, a region of interest is specified. While the B-mode image is being displayed, the controller controls the transmission frequency alteration section 401 of the transmission circuit 402 such that the transmission frequency is a B-mode frequency, and receives ultrasound signals from the ultrasound probe 300.

Next, in step S304, the transmission frequency is set to the transmission frequency for tissue characteristic diagnosis. For the transmission frequency for tissue characteristic diagnosis, as described above, for example, a frequency that is different than that for B-mode images and that is suited for diagnosing tissue characteristics is set in advance. The controller 100 controls the transmission frequency alteration section 401 such that the transmission frequency is changed.

In step S306, the transmission circuit 402 controls the ultrasound transducers in response to instructions from the controller 100, specifies a predetermined number of transmission focusing points along respective lines in the region of interest, and applies corresponding transmission focusing, and the reception circuit 404 receives signals via the respective elements. The RF signals received by the reception circuit 404 are converted to digital RF signals by the A/D converter 406.

In step S308, the data analysis and measurement section 106 specifies the predetermined number ($i_0$) of points of interest in the region of interest for the RF signals. There may be a single point of interest; that is, the predetermined number $i_0$ may be 1. By the processing described below, a variation index representing sound velocity variations or attenuation variations at the point of interest is found for each of the $i_0$ points of interest.

Firstly, in step S310, of the predetermined number ($i_0$) of points of interest in the region of interest for the RF signals, the data analysis and measurement section 106 sets the value i representing an identification number of a point of interest to 1 (i=1).

Then, in step S311, element reception data for a transmission focus corresponding to the point of interest with identification number i is selected, and a sound velocity or attenuation for the point of interest with identification number i is calculated from this data. A method for calculating the sound velocity or attenuation is not particularly limited; for example, the known method described below may be used.

For example, an image analysis technique that finds a sound velocity as a value at which a characteristic such as sharpness, contrast or the like in an image of a region of interest is at a maximum (for example, see JP-A No. 2007-7045) is known as a method of finding a sound velocity in a case in which an environmental sound velocity (average sound velocity) is used as the sound velocity at a point of interest.

Herein, a sound velocity that is assumed for specifying delay durations is referred to as "a specified sound velocity", and an intensity distribution of ultrasound intensities with respect to directional orientations is referred to as "a beam profile". A plural number of beam profiles for different specified sound velocities are generated from echo signals that have been subjected to phasing addition at the reception circuit, and the plural generated beam profiles are displayed superimposed in the same screen. From among the beam profiles with different specified sound velocities, the specified sound velocity of a beam profile that corresponds to a smallest beam width is estimated to be the environmental sound velocity.

Alternatively, a graph representing changes in beam width in accordance with specified sound velocities may be generated, and a minimum value of an approximation curve that approximates these changes with a high-order curve may be extracted. The specified sound velocity that corresponds to this minimum value may be estimated to be the environmental sound velocity.

The sound velocity at a point of interest may be a local sound velocity at the point of interest. Various methods are available for finding this local sound velocity. As one example, a method that finds the average sound velocity in a local region (the local sound velocity), described in the method of finding a variation index according to the first exemplary embodiment, may be used (for example, see JP-A No. 2010-99452).

As a method for finding the attenuation at a point of interest, for example, a method that finds the attenuation as follows, using the element reception signals before addition matching, may be considered.

For example, transmission focusing may be applied and a pseudo point reflection may be formed. Using element reception data therefrom, a distribution of the attenuation coefficient with respect to units of propagation duration may be found from changes, in the depth direction, in the central frequencies of signals received after addition matching is applied at the middle element or an aperture containing the middle element. Alternatively, a fact may be used that a central frequency of element reception signals is a value for which a central frequency of transmitted waves is shifted to the low-frequency side by an amount determined by the attenuation over a propagation distance that is determined by the depth of the pseudo point reflection and the element position. Therefore, the attenuation coefficient may be found from central frequencies of the element reception signals with three unknown values—the central frequency of the transmitted waves, the depth of the point reflection and the attenuation coefficient—or, when finding the sound velocity at the pseudo point reflection, the depth is found at the same time and the attenuation coefficient may be found with the central frequency of the transmitted waves being known.

In order to find the distribution of attenuation coefficients, the region of interest is specified, a predetermined number of transmission focusing points is specified along each of lines in the region of interest, the corresponding transmission focusing is applied, and signals are received at the elements. Then, a predetermined number of points of interest are specified with respect to directional positions and depth positions in the region of interest, and element reception signals for the transmission focusing corresponding to each point of interest are selected, from which the central frequency of a signal corresponding to the depth of the point of interest at the middle element is found. This is repeated in the depth position direction, differences between the central frequencies of points of interest in the depth direction are found, and the results are stored as attenuation coefficients. By repeating this for the respective point positions, attenuation coefficients with respect to units of propagation duration can be found. Alternatively, element reception signals for the transmission focusing corresponding to each point of interest are selected and, among the central frequency of the transmission wave, the depth of the point of interest and the attenuation coefficient, unknown quantities are adjusted and the attenuation coefficient that best matches the central frequencies of the element reception signals may be stored as the attenuation coefficient of the point of interest. This is repeated with respect to directional positions, whereby the distribution of attenuation coefficients may be found.

In order to find local attenuation coefficients from the central frequencies of the element reception signals, the region of interest is specified, a predetermined number of transmission focusing points are specified along each of lines in the region of interest, the corresponding transmission focusing is applied, and signals are received at the elements. Then, a predetermined number of points of interest are specified for directional positions and depth positions in the region of interest, a local region is specified with a point of interest disposed at the center of the upper face thereof, plural lattice points are specified at the lower face of the local region, and propagation paths from the point of interest through the lattice points to the elements are found. These propagation paths may be found when a local sound velocity in the local region is being found. Then, central frequencies at the lattice points along the lower face of the local region are found by reverse-shifting the central frequencies of the element reception signals for the transmission focusing corresponding to the point of interest along the paths from the lattice points to the elements. The shift amounts along the paths from the lattice points to the elements may be found from element reception signals that are obtained by separately applying transmission focusing corresponding to the lattice points. Meanwhile, because propagation path lengths from the lattice point directly below the point of interest→the point of interest→the respective lattice points have already been found when the local sound velocity has been found, the central frequency at a lattice point after propagation may be found from the central frequency and attenuation coefficient at the lattice point directly below the point of interest, by assuming that attenuation coefficients in the local region are uniform. The central frequency at the lattice point directly below the point of interest may be found from central frequencies that are obtained by separately applying transmission focusing corresponding to the lattice point directly below the point of interest. Hence, a residual between the central frequency of each lattice point found by assuming the attenuation coefficient and the central frequency of each lattice point found by reverse-shifting the central frequency from the element reception signals at the point of interest may be found, and an attenuation coefficient with which these residuals are minimized may be found to serve as the true value of the attenuation coefficient. Even in a case in which the central frequency at the lattice point directly below the point of interest is unknown, by adjusting two unknown quantities, the attenuation coefficient and the central frequency at the lattice point directly below the point of interest, the attenuation coefficient with which the central frequencies at the respective lattice points that are obtained best match the central frequencies at the lattice points that have been found by reverse-shifting the central frequencies may be used.

As described above, when the element reception data corresponding to a point of interest i and a local region are specified, a sound velocity or attenuation for the point of interest i can be found using the element reception data corresponding to lattice points specified along the lower face of the local region. How the lower face of the local region and the lattice points are specified is not particularly limited; the lower face may be specified along an arbitrary curved surface at the lower side of the point of interest. For example, the lower face may be specified along a boundary between tissues and lesions or the like.

In step S314, the data analysis and measurement section 106 increments the point of interest identification number i by 1 (1 is added to i). In step S316, a determination is made as to whether i exceeds the specified number of points of interest (the predetermined number $i_0$). If the result of this determination is that i has not exceeded $i_0$, the controller returns to step S312 and repeats the above-described processing to find the variation index representing sound velocity variations or attenuation variations at this point of interest i. If it is determined that i is above $i_0$, the controller proceeds on to step S317.

In step S317, the data analysis and measurement section 106 determines the variations index from the changes, at the region of interest, in the sound velocity or attenuation of the respective points of interest i, and displays the variations index on the display unit 104. Next, in step S320, the transmission frequency is returned to the transmission frequency for B-mode. Namely, the controller 100 controls the transmission frequency alteration section 401 such that the transmission frequency is changed to the transmission frequency for B-mode that has been set in advance, and the series of processings for determining the variations index for tissue characteristic diagnosis is ended.

An index based on the amounts of variations in sound velocity or attenuation in the region of interest, for example, a standard deviation, may be used as the variation index. Further, an index that is based on spatial frequencies of changes in sound velocity or attenuation at points of interest in the region of interest may be found, for example, by finding a two-dimensional frequency distribution of sound velocities or attenuations and finding the index from the central frequency, bandwidth or skew of the two-dimensional frequency distribution.

Alternatively, various other indices with which non-uniformity may be evaluated can be considered as variation indices. For example, a characteristic quantity—skew, kurtosis or the like—of the shape of a histogram of a sound velocity or attenuation distribution in a region of interest, or of a spatial frequency distribution of the same, may be used as the variation index, or a texture characteristic quantity—for example, uniformity, contrast, correlation, entropy or the like—of texture according to a concurrent matrix or the like may be used as the variation index. Rather than using a single such characteristic quantity as the variation index, multiple regression from plural characteristic quantities may be used as the variation index.

Thus, an index that represents variations in sound velocity or attenuation (the variation index) may be calculated, and hence this index may be used to diagnose a tissue characteristic.

Moreover, at the time of carrying out diagnosis of tissue characteristics, in the same way as in the first embodiment, diagnosis is carried out by changing to a frequency that is suited to the diagnosis of tissue characteristics. Therefore, non-uniformity of micro-structures can be measured highly accurately.

Note that, in the above-described first embodiment and second embodiment, different transmission frequencies are used for the B-mode and for tissue characteristic diagnosis. However, embodiments are not limited to this, and may be made such that the reception frequency is changed. For example, an example of a case of changing the reception frequency with respect to the first embodiment is described hereinafter. Note that although a case of changing the reception frequency with respect to the first embodiment is described hereinafter, the reception frequency may be changed with respect to the second embodiment.

The reception frequency may be changed by transmitting wide band frequency ultrasound waves by the wide band frequency ultrasound transducers 302, providing a reception frequency alteration section at the receiving circuit 404, and changing the reception frequency by the reception frequency alteration section. The reception frequency alteration section may change the reception frequency by, for example, using filters such as band pass filters or the like. Namely, plural types of band pass filters (e.g., band pass filters that pass-through predetermined frequencies for B-mode, or band pass filters that pass-through predetermined frequencies in accordance with the depth and size of the region to be observed (the organ to be observed or lesion), or the like) are provided as the receiving frequency alteration section at the receiving circuit 404. By changing the band pass filter that is used by control of the controller 100, signals of a desired frequency can be obtained from wide band frequency ultrasound signals.

Figure 11:
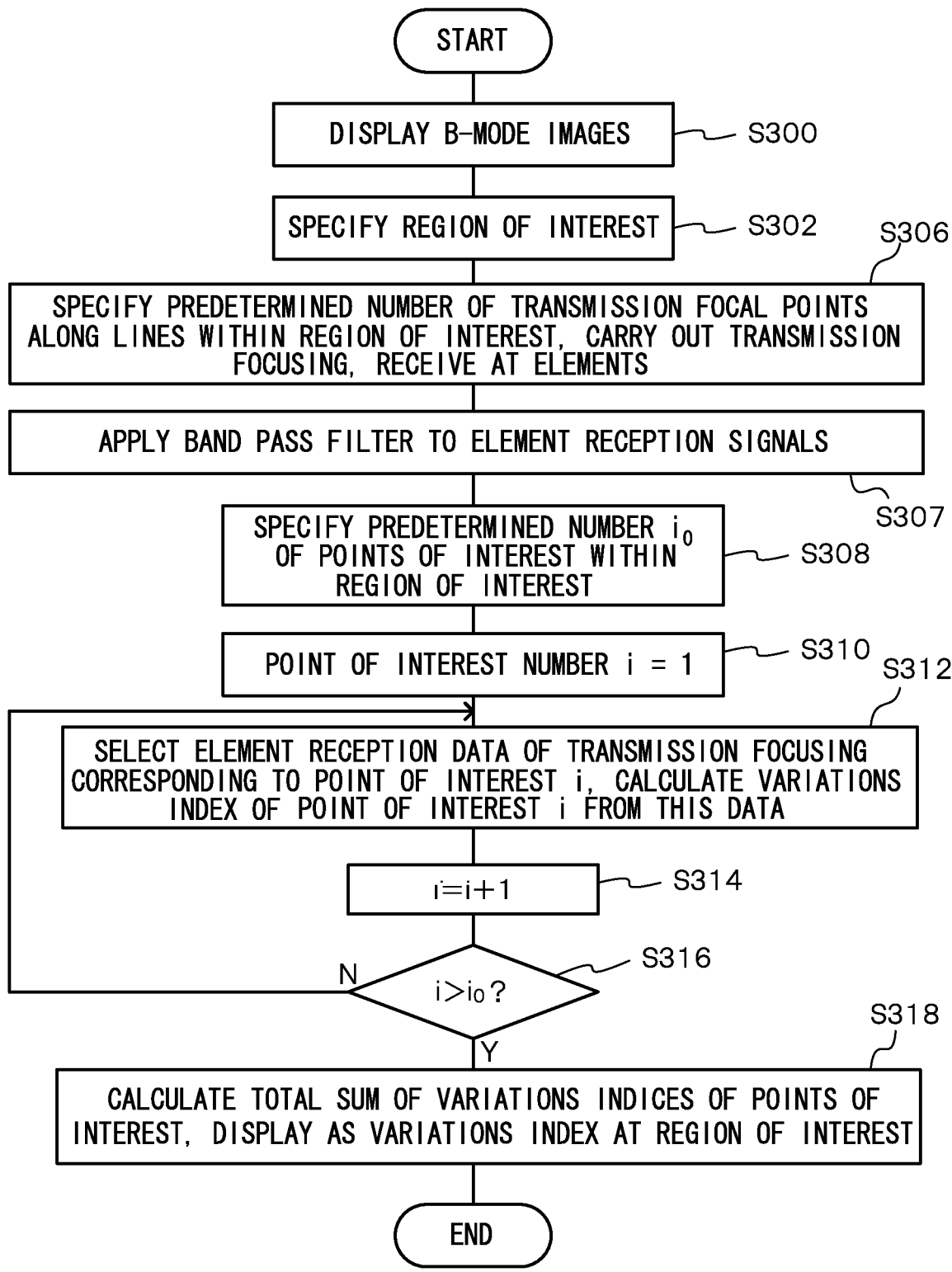
FIG. 11 is a flowchart showing an example of the flow of an overall flow of processing to calculate a variation index representing sound velocity variations or attenuation variations, which is executed by a controller of an ultrasound diagnostic device in which a reception frequency is alterable.

FIG. 11 is a flowchart showing an example of the overall flow of processing to calculate variation indices representing sound velocity variations or attenuation variations, which is executed by the controller 100 of the ultrasound diagnostic device in which the reception frequency is alterable. Processing that is the same as in the first exemplary embodiment is assigned the same reference numerals in FIG. 11 and is only briefly described.

First, in step S300, a B-mode image is displayed. Then, in step S302, a region of interest is specified. While the B-mode image is being displayed, the controller 100 controls the reception circuit 404 such that the reception frequency is a B-mode frequency and receives ultrasound signals from the ultrasound probe 300.

In step S306, the transmission circuit 402 controls the ultrasound transducers in response to instructions from the controller 100, specifies a predetermined number of transmission focusing points along respective lines in the region of interest, and applies corresponding transmission focusing, and the reception circuit 404 receives signals via the respective elements.

Next, in step S307, band pass filtering is applied to the received signals of the respective elements. Namely, the controller 100 controls the receiving circuit 404, and selects the band pass filter for making the received signals be received signals of a frequency for tissue characteristic diagnosis, and makes the received signals be a frequency for tissue characteristic diagnosis. The RF signals received by the receiving circuit 404 are converted into digital RF signals by the A/D converter 406.

In step S308, the data analysis and measurement section 106 specifies the predetermined number ($i_0$) of points of interest in the region of interest for the RF signals. In step S310, of the predetermined number ($i_0$) of points of interest in the region of interest for the RF signals, the data analysis and measurement section 106 sets the value i representing an identification number of a point of interest to 1 (i=1).

In step S312, element reception data for a transmission focus corresponding to the point of interest with identification number i is selected, and the variation index representing sound velocity variations or attenuation variations for the point of interest with identification number i is calculated from this data.

In step S314, the data analysis and measurement section 106 increments the point of interest identification number i by 1 (1 is added to i). In step S316, a determination is made as to whether i exceeds the specified number of points of interest (the predetermined number $i_0$). If the result of this determination is that i has not exceeded $i_0$, the processing returns to step S312 and repeats the above-described processing to find the variation index representing sound velocity variations or attenuation variations at this point of interest i. If it is determined that i is above $i_0$, the controller 100 proceeds on to step S318.

Then, in step S318, the data analysis and measurement section 106 calculates the total sum of the variations indices of the respective points of interest i, and displays this on the display unit 104 as the variations index at the region of interest, and ends the series of processings for determining the variations index for diagnosing tissue characteristics.

By changing the reception frequency in this way, non-uniformity of micro-structures may also be measured highly accurately in the same way as in the first embodiment.

Hereabove, an ultrasound diagnostic device and ultrasound diagnostic method have been described in detail in accordance with the embodiments. However, embodiments are not limited to the above examples, and it will be clear that numerous modifications and improvements may be applied within a scope not departing from the spirit of the present invention.

The processing performed by the controller 100 in the exemplary embodiments described above may be stored as a program and distributed on various kinds of non-transitory storage media.

What is claimed is:

1. An ultrasound diagnostic device comprising:
   an ultrasound probe including a plurality of ultrasound transducers that transmit ultrasound toward an imaging subject, receive ultrasound reflected from the imaging subject, and output ultrasound detection signals;
   a memory; and
   processor coupled to the memory, the processor configured to
   set a transmission frequency of the ultrasound transmitted from the ultrasound probe or a reception frequency of the ultrasound received by the ultrasound probe to a first frequency that is used in a case of converting amplitudes, of the ultrasound detection signals outputted from the ultrasound probe, into an intensity distribution of brightness;
   generate a brightness image using the intensity distribution of the brightness and display the brightness image;
   receive a user's designation of a region to be observed on the brightness image;
   alter the transmission frequency of the ultrasound transmitted from the ultrasound probe or the reception frequency of the ultrasound detection signals received by the ultrasound probe to a second frequency that is set in advance in accordance with a size of the received region to be observed, in order to diagnose tissue characteristics;
   calculate an index for diagnosing tissue characteristics, based on a relationship between received signals, at the time when the transmission frequency or the reception frequency is altered by the processor to the second frequency at which diagnosis of tissue characteristics is carried out, at two or more different ultrasound transducers of the plurality of ultrasound transducers.

2. The ultrasound diagnostic device of claim 1, wherein the processor is configured to calculate the index by evaluating non-uniformity of an acoustic characteristic based on the relationship between the received signals of the two or more ultrasound transducers whose ultrasound differ at the received region.

3. The ultrasound diagnostic device of claim 1, wherein the processor is configured to determine sound velocity or attenuation at least at one point of interest within the received region, and calculates the index based on the determined sound velocity or attenuation.

4. The ultrasound diagnostic device of claim 1, further comprising a display unit that displays the calculated index.

5. An ultrasound diagnostic method comprising:
   employing a processor to set a transmission frequency of ultrasound transmitted from an ultrasound probe that includes a plurality of ultrasound transducers that transmit ultrasound toward an imaging subject, receive ultrasound reflected from the imaging subject, and output ultrasound detection signals, or set a reception frequency of ultrasound received by the ultrasound probe, to a first frequency that is used in a case of converting amplitudes of the ultrasound detection signals outputted from the ultrasound probe into an intensity distribution of brightness;

generating a brightness image using the intensity distribution of the brightness and displaying the brightness image;

receiving a user's designation of a region to be observed on the brightness image;

alter the transmission frequency of the ultrasound transmitted from the ultrasound probe or the reception frequency of the ultrasound detection signals received by the ultrasound probe to a second frequency that is set in advance in accordance with a size of the received region to be observed, in order to diagnose tissue characteristics;

calculating an index for diagnosing tissue characteristics, based on a relationship between received signals, at the time when the transmission frequency or the reception frequency is altered to the second frequency used for carrying out diagnosis of tissue characteristics, at two or more different ultrasound transducers of the plurality of ultrasound transducers.

6. The ultrasound diagnostic method of claim 5, wherein the calculation includes calculating the index by evaluating non-uniformity of an acoustic characteristic based on the relationship of the received signals of the two or more ultrasound transducers whose ultrasound differ at the received region.

7. The ultrasound diagnostic method of claim 5, wherein the calculation includes determining sound velocity or attenuation at least at one point of interest within the received region, and calculating the index based on the determined sound velocity or attenuation.

8. The ultrasound diagnostic method of claim 5, further comprising displaying, at a display unit, the calculated index.

9. A non-transitory storage medium storing a program that causes a computer comprising a processor to execute ultrasound diagnostic processings, the processings comprising:

employing the processor to set a transmission frequency of ultrasound transmitted from an ultrasound probe that includes a plurality of ultrasound transducers that transmit ultrasound toward an imaging subject, receive ultrasound reflected from the imaging subject, and output ultrasound detection signals, or a reception frequency of ultrasound received by the ultrasound probe, to a first frequency that is used in a case of converting amplitudes of the ultrasound detection signals outputted from the ultrasound probe into an intensity distribution of brightness;

generating a brightness image using the intensity distribution of the brightness and controlling the display unit to display the brightness image;

receiving a user's designation of a region to be observed on the brightness image;

altering the transmission frequency of the ultrasound transmitted from the ultrasound probe or the reception frequency of the ultrasound detection signals received by the ultrasound probe to a second frequency that is set in advance in accordance with a size of the received region to be observed, in order to diagnose tissue characteristics;

calculating an index for diagnosing tissue characteristics, based on a relationship between received signals, at the time when the transmission frequency or the reception frequency is altered to the second frequency used for carrying out diagnosis of tissue characteristics, at two or more different ultrasound transducers of the plurality of ultrasound transducers.

10. The non-transitory storage medium of claim 9, wherein the calculation includes calculating the index by evaluating non-uniformity of an acoustic characteristic based on the relationship between the received signals of the two or more ultrasound transducers whose ultrasound differ at the received region.

11. The non-transitory storage medium of claim 9, wherein the calculation includes determining sound velocity or attenuation at least at one point of interest within the received region, and calculating the index based on the determined sound velocity or attenuation.

12. The non-transitory storage medium of claim 9, further comprising controlling the display unit to display, the computed index.

* * * * *